United States Patent
Yu et al.

(10) Patent No.: US 11,187,703 B2
(45) Date of Patent: Nov. 30, 2021

(54) METHOD FOR CANCER DIAGNOSIS AND PROGNOSIS

(71) Applicants: Chang Gung University, Taoyuan (TW); Linkou Chang Gung Memorial Hospital, Taoyuan (TW)

(72) Inventors: Jau-Song Yu, Taoyuan (TW); Yi-Ting Chen, Taoyuan (TW); Wei-Fan Chiang, Tainan (TW); Yung-Chin Hsiao, New Taipei (TW); Yu-Sun Chang, San Francisco, CA (US); Lai-Chu See, Taoyuan (TW); Kai-Ping Chang, Taipei (TW)

(73) Assignee: S&T BIOMED CO., LTD., Hsinchu County (TW)

( * ) Notice: Subject to any disclaimer, the term of this patent is extended or adjusted under 35 U.S.C. 154(b) by 583 days.

(21) Appl. No.: 16/084,239

(22) PCT Filed: Mar. 17, 2017

(86) PCT No.: PCT/US2017/022853
§ 371 (c)(1),
(2) Date: Sep. 12, 2018

(87) PCT Pub. No.: WO2017/161215
PCT Pub. Date: Sep. 21, 2017

(65) Prior Publication Data
US 2019/0056400 A1    Feb. 21, 2019

Related U.S. Application Data

(60) Provisional application No. 62/309,766, filed on Mar. 17, 2016.

(51) Int. Cl.
*G01N 33/574* (2006.01)
*G01N 30/72* (2006.01)
(Continued)

(52) U.S. Cl.
CPC ... *G01N 33/57407* (2013.01); *G01N 30/7233* (2013.01); *G01N 33/6848* (2013.01);
(Continued)

(58) Field of Classification Search
CPC ......... G01N 30/7233; G01N 33/57407; G01N 33/6848; G01N 2030/027; G01N 2458/15;
(Continued)

(56) References Cited

PUBLICATIONS

Kirkpatrick et al. (Methods, 2005, pp. 265-273) (Year: 2005).*
(Continued)

*Primary Examiner* — Jeremy C Flinders

(57) ABSTRACT

Disclosed herein is a method of determining whether a subject has or is at risk of developing a cancer. The method comprises, obtaining a sample from the subject; determining the levels of at least two target polypeptides, which are selected from the group consisting of, ANXA2, HSPA5, KNG1 and MMP1; and assessing whether the subject has or is at risk of developing the cancer based on the levels of target polypeptides. The present method provides a potential means to diagnose and predict the occurrence of oral squamous cell carcinoma, and accordingly, the subject in need thereof could receive a suitable therapeutic regimen in time.

15 Claims, 3 Drawing Sheets

Specification includes a Sequence Listing.

(51) Int. Cl.
*G01N 33/68* (2006.01)
*G16B 40/00* (2019.01)
*G01N 30/02* (2006.01)

(52) U.S. Cl.
CPC ....... *G16B 40/00* (2019.02); *G01N 2030/027* (2013.01); *G01N 2458/15* (2013.01); *G01N 2800/50* (2013.01); *G01N 2800/52* (2013.01)

(58) Field of Classification Search
CPC . G01N 2800/50; G01N 2800/52; G16B 40/00
See application file for complete search history.

(56) References Cited

PUBLICATIONS

Thermo Scientific ("Protein Quantification Using Mass Spectrometry" brochure_ (Year: 2014).*
Kashyap et al. (Cancer Biology & Therapy, 2010, 10(8):796-810) (Year: 2010).*

* cited by examiner

SEQUENCE LISTING

<160> NUMBER OF SEQ ID NOS: 8

<210> SEQ ID NO 1
<211> LENGTH: 339
<212> TYPE: PRT
<213> ORGANISM: Artificial Sequence
<220> FEATURE:
<223> OTHER INFORMATION: ANXA2 polypeptide

<400> SEQUENCE: 1

```
Met Ser Thr Val His Glu Ile Leu Cys Lys Leu Ser Leu Glu Gly Asp
1               5                   10                  15

His Ser Thr Pro Pro Ser Ala Tyr Gly Ser Val Lys Ala Tyr Thr Asn
            20                  25                  30

Phe Asp Ala Glu Arg Asp Ala Leu Asn Ile Glu Thr Ala Ile Lys Thr
        35                  40                  45

Lys Gly Val Asp Glu Val Thr Ile Val Asn Ile Leu Thr Asn Arg Ser
    50                  55                  60

Asn Ala Gln Arg Gln Asp Ile Ala Phe Ala Tyr Gln Arg Arg Thr Lys
65                  70                  75                  80

Lys Glu Leu Ala Ser Ala Leu Lys Ser Ala Leu Ser Gly His Leu Glu
                85                  90                  95

Thr Val Ile Leu Gly Leu Leu Lys Thr Pro Ala Gln Tyr Asp Ala Ser
            100                 105                 110

Glu Leu Lys Ala Ser Met Lys Gly Leu Gly Thr Asp Glu Asp Ser Leu
        115                 120                 125

Ile Glu Ile Ile Cys Ser Arg Thr Asn Gln Glu Leu Gln Glu Ile Asn
    130                 135                 140

Arg Val Tyr Lys Glu Met Tyr Lys Thr Asp Leu Glu Lys Asp Ile Ile
145                 150                 155                 160

Ser Asp Thr Ser Gly Asp Phe Arg Lys Leu Met Val Ala Leu Ala Lys
                165                 170                 175

Gly Arg Arg Ala Glu Asp Gly Ser Val Ile Asp Tyr Glu Leu Ile Asp
            180                 185                 190

Gln Asp Ala Arg Asp Leu Tyr Asp Ala Gly Val Lys Arg Lys Gly Thr
        195                 200                 205

Asp Val Pro Lys Trp Ile Ser Ile Met Thr Glu Arg Ser Val Pro His
    210                 215                 220

Leu Gln Lys Val Phe Asp Arg Tyr Lys Ser Tyr Ser Pro Tyr Asp Met
225                 230                 235                 240

Leu Glu Ser Ile Arg Lys Glu Val Lys Gly Asp Leu Glu Asn Ala Phe
                245                 250                 255

Leu Asn Leu Val Gln Cys Ile Gln Asn Lys Pro Leu Tyr Phe Ala Asp
            260                 265                 270

Arg Leu Tyr Asp Ser Met Lys Gly Lys Gly Thr Arg Asp Lys Val Leu
        275                 280                 285

Ile Arg Ile Met Val Ser Arg Ser Glu Val Asp Met Leu Lys Ile Arg
    290                 295                 300

Ser Glu Phe Lys Arg Lys Tyr Gly Lys Ser Leu Tyr Tyr Tyr Ile Gln
305                 310                 315                 320

Gln Asp Thr Lys Gly Asp Tyr Gln Lys Ala Leu Leu Tyr Leu Cys Gly
                325                 330                 335

Gly Asp Asp
```

<210> SEQ ID NO 2

```
<211> LENGTH: 654
<212> TYPE: PRT
<213> ORGANISM: Artificial Sequence
<220> FEATURE:
<223> OTHER INFORMATION: HSPA5 polypeptide

<400> SEQUENCE: 2

Met Lys Leu Ser Leu Val Ala Ala Met Leu Leu Leu Leu Ser Ala Ala
1               5                   10                  15

Arg Ala Glu Glu Glu Asp Lys Lys Glu Asp Val Gly Thr Val Val Gly
            20                  25                  30

Ile Asp Leu Gly Thr Thr Tyr Ser Cys Val Gly Val Phe Lys Asn Gly
        35                  40                  45

Arg Val Glu Ile Ile Ala Asn Asp Gln Gly Asn Arg Ile Thr Pro Ser
50                  55                  60

Tyr Val Ala Phe Thr Pro Glu Gly Glu Arg Leu Ile Gly Asp Ala Ala
65                  70                  75                  80

Lys Asn Gln Leu Thr Ser Asn Pro Glu Asn Thr Val Phe Asp Ala Lys
                85                  90                  95

Arg Leu Ile Gly Arg Thr Trp Asn Asp Pro Ser Val Gln Gln Asp Ile
            100                 105                 110

Lys Phe Leu Pro Phe Lys Val Val Glu Lys Lys Thr Lys Pro Tyr Ile
        115                 120                 125

Gln Val Asp Ile Gly Gly Gly Gln Thr Lys Thr Phe Ala Pro Glu Glu
130                 135                 140

Ile Ser Ala Met Val Leu Thr Lys Met Lys Glu Thr Ala Glu Ala Tyr
145                 150                 155                 160

Leu Gly Lys Lys Val Thr His Ala Val Val Thr Val Pro Ala Tyr Phe
                165                 170                 175

Asn Asp Ala Gln Arg Gln Ala Thr Lys Asp Ala Gly Thr Ile Ala Gly
            180                 185                 190

Leu Asn Val Met Arg Ile Ile Asn Glu Pro Thr Ala Ala Ala Ile Ala
        195                 200                 205

Tyr Gly Leu Asp Lys Arg Glu Gly Glu Lys Asn Ile Leu Val Phe Asp
210                 215                 220

Leu Gly Gly Gly Thr Phe Asp Val Ser Leu Leu Thr Ile Asp Asn Gly
225                 230                 235                 240

Val Phe Glu Val Val Ala Thr Asn Gly Asp Thr His Leu Gly Gly Glu
                245                 250                 255

Asp Phe Asp Gln Arg Val Met Glu His Phe Ile Lys Leu Tyr Lys Lys
            260                 265                 270

Lys Thr Gly Lys Asp Val Arg Lys Asp Asn Arg Ala Val Gln Lys Leu
        275                 280                 285

Arg Arg Glu Val Glu Lys Ala Lys Arg Ala Leu Ser Ser Gln His Gln
290                 295                 300

Ala Arg Ile Glu Ile Glu Ser Phe Tyr Glu Gly Glu Asp Phe Ser Glu
305                 310                 315                 320

Thr Leu Thr Arg Ala Lys Phe Glu Glu Leu Asn Met Asp Leu Phe Arg
                325                 330                 335

Ser Thr Met Lys Pro Val Gln Lys Val Leu Glu Asp Ser Asp Leu Lys
            340                 345                 350

Lys Ser Asp Ile Asp Glu Ile Val Leu Val Gly Gly Ser Thr Arg Ile
        355                 360                 365

Pro Lys Ile Gln Gln Leu Val Lys Glu Phe Phe Asn Gly Lys Glu Pro
370                 375                 380
```

```
Ser Arg Gly Ile Asn Pro Asp Glu Ala Val Ala Tyr Gly Ala Val
385                 390                 395                 400

Gln Ala Gly Val Leu Ser Asp Gln Asp Thr Gly Asp Leu Val Leu
            405                 410                 415

Leu Asp Val Cys Pro Leu Thr Leu Gly Ile Glu Thr Val Gly Gly Val
            420                 425                 430

Met Thr Lys Leu Ile Pro Arg Asn Thr Val Pro Thr Lys Lys Ser
            435                 440                 445

Gln Ile Phe Ser Thr Ala Ser Asp Asn Gln Pro Thr Val Thr Ile Lys
            450                 455                 460

Val Tyr Glu Gly Glu Arg Pro Leu Thr Lys Asp Asn His Leu Leu Gly
465                 470                 475                 480

Thr Phe Asp Leu Thr Gly Ile Pro Pro Ala Pro Arg Gly Val Pro Gln
            485                 490                 495

Ile Glu Val Thr Phe Glu Ile Asp Val Asn Gly Ile Leu Arg Val Thr
            500                 505                 510

Ala Glu Asp Lys Gly Thr Gly Asn Lys Asn Lys Ile Thr Ile Thr Asn
            515                 520                 525

Asp Gln Asn Arg Leu Thr Pro Glu Glu Ile Glu Arg Met Val Asn Asp
530                 535                 540

Ala Glu Lys Phe Ala Glu Glu Asp Lys Lys Leu Lys Glu Arg Ile Asp
545                 550                 555                 560

Thr Arg Asn Glu Leu Glu Ser Tyr Ala Tyr Ser Leu Lys Asn Gln Ile
            565                 570                 575

Gly Asp Lys Glu Lys Leu Gly Gly Lys Leu Ser Ser Glu Asp Lys Glu
            580                 585                 590

Thr Met Glu Lys Ala Val Glu Glu Lys Ile Glu Trp Leu Glu Ser His
            595                 600                 605

Gln Asp Ala Asp Ile Glu Asp Phe Lys Ala Lys Lys Lys Glu Leu Glu
            610                 615                 620

Glu Ile Val Gln Pro Ile Ile Ser Lys Leu Tyr Gly Ser Ala Gly Pro
625                 630                 635                 640

Pro Pro Thr Gly Glu Glu Asp Thr Ala Glu Lys Asp Glu Leu
            645                 650

<210> SEQ ID NO 3
<211> LENGTH: 644
<212> TYPE: PRT
<213> ORGANISM: Artificial Sequence
<220> FEATURE:
<223> OTHER INFORMATION: KNG1 polypeptide

<400> SEQUENCE: 3

Met Lys Leu Ile Thr Ile Leu Phe Leu Cys Ser Arg Leu Leu Leu Ser
1               5                   10                  15

Leu Thr Gln Glu Ser Gln Ser Glu Glu Ile Asp Cys Asn Asp Lys Asp
            20                  25                  30

Leu Phe Lys Ala Val Asp Ala Ala Leu Lys Lys Tyr Asn Ser Gln Asn
            35                  40                  45

Gln Ser Asn Asn Gln Phe Val Leu Tyr Arg Ile Thr Glu Ala Thr Lys
    50                  55                  60

Thr Val Gly Ser Asp Thr Phe Tyr Ser Phe Lys Tyr Glu Ile Lys Glu
65              70                  75                  80

Gly Asp Cys Pro Val Gln Ser Gly Lys Thr Trp Gln Asp Cys Glu Tyr
            85                  90                  95
```

```
Lys Asp Ala Ala Lys Ala Ala Thr Gly Glu Cys Thr Ala Thr Val Gly
            100                 105                 110

Lys Arg Ser Ser Thr Lys Phe Ser Val Ala Thr Gln Thr Cys Gln Ile
            115                 120                 125

Thr Pro Ala Glu Gly Pro Val Val Thr Ala Gln Tyr Asp Cys Leu Gly
        130                 135                 140

Cys Val His Pro Ile Ser Thr Gln Ser Pro Asp Leu Glu Pro Ile Leu
145                 150                 155                 160

Arg His Gly Ile Gln Tyr Phe Asn Asn Thr Gln His Ser Ser Leu
                165                 170                 175

Phe Met Leu Asn Glu Val Lys Arg Ala Gln Arg Gln Val Val Ala Gly
            180                 185                 190

Leu Asn Phe Arg Ile Thr Tyr Ser Ile Val Gln Thr Asn Cys Ser Lys
            195                 200                 205

Glu Asn Phe Leu Phe Leu Thr Pro Asp Cys Lys Ser Leu Trp Asn Gly
            210                 215                 220

Asp Thr Gly Glu Cys Thr Asp Asn Ala Tyr Ile Asp Ile Gln Leu Arg
225                 230                 235                 240

Ile Ala Ser Phe Ser Gln Asn Cys Asp Ile Tyr Pro Gly Lys Asp Phe
                245                 250                 255

Val Gln Pro Pro Thr Lys Ile Cys Val Gly Cys Pro Arg Asp Ile Pro
            260                 265                 270

Thr Asn Ser Pro Glu Leu Glu Glu Thr Leu Thr His Thr Ile Thr Lys
            275                 280                 285

Leu Asn Ala Glu Asn Asn Ala Thr Phe Tyr Phe Lys Ile Asp Asn Val
            290                 295                 300

Lys Lys Ala Arg Val Gln Val Val Ala Gly Lys Lys Tyr Phe Ile Asp
305                 310                 315                 320

Phe Val Ala Arg Glu Thr Thr Cys Ser Lys Glu Ser Asn Glu Glu Leu
                325                 330                 335

Thr Glu Ser Cys Glu Thr Lys Lys Leu Gly Gln Ser Leu Asp Cys Asn
            340                 345                 350

Ala Glu Val Tyr Val Val Pro Trp Glu Lys Lys Ile Tyr Pro Thr Val
            355                 360                 365

Asn Cys Gln Pro Leu Gly Met Ile Ser Leu Met Lys Arg Pro Pro Gly
370                 375                 380

Phe Ser Pro Phe Arg Ser Ser Arg Ile Gly Glu Ile Lys Glu Glu Thr
385                 390                 395                 400

Thr Val Ser Pro Pro His Thr Ser Met Ala Pro Ala Gln Asp Glu Glu
            405                 410                 415

Arg Asp Ser Gly Lys Glu Gln Gly His Thr Arg Arg His Asp Trp Gly
            420                 425                 430

His Glu Lys Gln Arg Lys His Asn Leu Gly His Gly His Lys His Glu
            435                 440                 445

Arg Asp Gln Gly His Gly His Gln Arg Gly His Gly Leu Gly His Gly
        450                 455                 460

His Glu Gln Gln His Gly Leu Gly His Gly His Lys Phe Lys Leu Asp
465                 470                 475                 480

Asp Asp Leu Glu His Gln Gly Gly His Val Leu Asp His Gly His Lys
            485                 490                 495

His Lys His Gly His Gly His Gly Lys His Lys Asn Lys Gly Lys Lys
            500                 505                 510
```

Asn Gly Lys His Asn Gly Trp Lys Thr Glu His Leu Ala Ser Ser Ser
        515                 520                 525

Glu Asp Ser Thr Thr Pro Ser Ala Gln Thr Gln Glu Lys Thr Glu Gly
        530                 535                 540

Pro Thr Pro Ile Pro Ser Leu Ala Lys Pro Gly Val Thr Val Thr Phe
545                 550                 555                 560

Ser Asp Phe Gln Asp Ser Asp Leu Ile Ala Thr Met Met Pro Pro Ile
                565                 570                 575

Ser Pro Ala Pro Ile Gln Ser Asp Asp Trp Ile Pro Asp Ile Gln
                580                 585                 590

Ile Asp Pro Asn Gly Leu Ser Phe Asn Pro Ile Ser Asp Phe Pro Asp
        595                 600                 605

Thr Thr Ser Pro Lys Cys Pro Gly Arg Pro Trp Lys Ser Val Ser Glu
        610                 615                 620

Ile Asn Pro Thr Thr Gln Met Lys Glu Ser Tyr Tyr Phe Asp Leu Thr
625                 630                 635                 640

Asp Gly Leu Ser

<210> SEQ ID NO 4
<211> LENGTH: 469
<212> TYPE: PRT
<213> ORGANISM: Artificial Sequence
<220> FEATURE:
<223> OTHER INFORMATION: MMP1 polypeptide

<400> SEQUENCE: 4

Met His Ser Phe Pro Pro Leu Leu Leu Leu Phe Trp Gly Val Val
1               5                   10                  15

Ser His Ser Phe Pro Ala Thr Leu Glu Thr Gln Glu Gln Asp Val Asp
                20                  25                  30

Leu Val Gln Lys Tyr Leu Glu Lys Tyr Tyr Asn Leu Lys Asn Asp Gly
        35                  40                  45

Arg Gln Val Glu Lys Arg Arg Asn Ser Gly Pro Val Val Glu Lys Leu
    50                  55                  60

Lys Gln Met Gln Glu Phe Phe Gly Leu Lys Val Thr Gly Lys Pro Asp
65                  70                  75                  80

Ala Glu Thr Leu Lys Val Met Lys Gln Pro Arg Cys Gly Val Pro Asp
                85                  90                  95

Val Ala Gln Phe Val Leu Thr Glu Gly Asn Pro Arg Trp Glu Gln Thr
            100                 105                 110

His Leu Thr Tyr Arg Ile Glu Asn Tyr Thr Pro Asp Leu Pro Arg Ala
        115                 120                 125

Asp Val Asp His Ala Ile Glu Lys Ala Phe Gln Leu Trp Ser Asn Val
    130                 135                 140

Thr Pro Leu Thr Phe Thr Lys Val Ser Glu Gly Gln Ala Asp Ile Met
145                 150                 155                 160

Ile Ser Phe Val Arg Gly Asp His Arg Asp Asn Ser Pro Phe Asp Gly
                165                 170                 175

Pro Gly Gly Asn Leu Ala His Ala Phe Gln Pro Gly Pro Gly Ile Gly
            180                 185                 190

Gly Asp Ala His Phe Asp Glu Asp Glu Arg Trp Thr Asn Asn Phe Arg
        195                 200                 205

Glu Tyr Asn Leu His Arg Val Ala Ala His Glu Leu Gly His Ser Leu
    210                 215                 220

Gly Leu Ser His Ser Thr Asp Ile Gly Ala Leu Met Tyr Pro Ser Tyr

-continued

```
            225                 230                 235                 240

Thr Phe Ser Gly Asp Val Gln Leu Ala Gln Asp Asp Ile Asp Gly Ile
                    245                 250                 255

Gln Ala Ile Tyr Gly Arg Ser Gln Asn Pro Val Gln Pro Ile Gly Pro
                    260                 265                 270

Gln Thr Pro Lys Ala Cys Asp Ser Lys Leu Thr Phe Asp Ala Ile Thr
                    275                 280                 285

Thr Ile Arg Gly Glu Val Met Phe Phe Lys Asp Arg Phe Tyr Met Arg
                    290                 295                 300

Thr Asn Pro Phe Tyr Pro Glu Val Glu Leu Asn Phe Ile Ser Val Phe
        305                 310                 315                 320

Trp Pro Gln Leu Pro Asn Gly Leu Glu Ala Ala Tyr Glu Phe Ala Asp
                    325                 330                 335

Arg Asp Glu Val Arg Phe Phe Lys Gly Asn Lys Tyr Trp Ala Val Gln
                    340                 345                 350

Gly Gln Asn Val Leu His Gly Tyr Pro Lys Asp Ile Tyr Ser Ser Phe
                    355                 360                 365

Gly Phe Pro Arg Thr Val Lys His Ile Asp Ala Ala Leu Ser Glu Glu
                    370                 375                 380

Asn Thr Gly Lys Thr Tyr Phe Phe Val Ala Asn Lys Tyr Trp Arg Tyr
        385                 390                 395                 400

Asp Glu Tyr Lys Arg Ser Met Asp Pro Gly Tyr Pro Lys Met Ile Ala
                    405                 410                 415

His Asp Phe Pro Gly Ile Gly His Lys Val Asp Ala Val Phe Met Lys
                    420                 425                 430

Asp Gly Phe Phe Tyr Phe Phe His Gly Thr Arg Gln Tyr Lys Phe Asp
                    435                 440                 445

Pro Lys Thr Lys Arg Ile Leu Thr Leu Gln Lys Ala Asn Ser Trp Phe
                    450                 455                 460

Asn Cys Arg Lys Asn
        465

<210> SEQ ID NO 5
<211> LENGTH: 9
<212> TYPE: PRT
<213> ORGANISM: Artificial Sequence
<220> FEATURE:
<223> OTHER INFORMATION: SIS peptide for ANXA2

<400> SEQUENCE: 5

Gln Asp Ile Ala Phe Ala Tyr Gln Arg
1               5

<210> SEQ ID NO 6
<211> LENGTH: 14
<212> TYPE: PRT
<213> ORGANISM: Artificial Sequence
<220> FEATURE:
<223> OTHER INFORMATION: SIS peptide for HSPA5

<400> SEQUENCE: 6

Ile Thr Pro Ser Tyr Val Ala Phe Thr Pro Glu Gly Glu Arg
1               5                   10

<210> SEQ ID NO 7
<211> LENGTH: 11
<212> TYPE: PRT
<213> ORGANISM: Artificial Sequence
<220> FEATURE:
```

```
<223> OTHER INFORMATION: SIS peptide for KNG1

<400> SEQUENCE: 7

Thr Val Gly Ser Asp Thr Phe Tyr Ser Phe Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: SIS peptide for MMP1

<400> SEQUENCE: 8

Asp Ile Tyr Ser Ser Phe Gly Phe Pro Arg
1               5                   10
```

METHOD FOR CANCER DIAGNOSIS AND PROGNOSIS

CROSS-REFERENCE TO RELATED APPLICATIONS

This application relates to and claims the benefit of U.S. Provisional Application No. 62/309,766, filed Mar. 17, 2016; the content of the application is incorporated herein by reference in its entirety.

BACKGROUND OF THE INVENTION

1. Field of the Invention

The present invention relates to a multiple-markers panel for detecting oral squamous cell carcinoma (OSCC), and more particularly to, a four-protein panel, a three-protein panel or a two-protein panel, which offers a tool for detecting OSCC and monitoring patients with oral potentially malignant disorders (OPMDs), using saliva samples.

2. Description of the Related Art

Oral cavity cancer is a common cancer worldwide and represents a serious and growing problem in many parts of the globe. The tongue and buccal regions are the most common sites for intraoral cancer among European/American and Asian populations, respectively. An estimated 300,400 new cases of oral cancer and 145,400 oral cancer-related deaths occurred worldwide in 2012. The highest incidence rates were recorded in Melanesia, South-Central Asia, and Central and Eastern Europe (9.1~22.9 per 100,000). More than one-third of the new cases and half of the deaths were reported in developing countries. However, the incidence continues to rise in the West, with the age-standardized incidence of oral cancer in Western Europe showing a steady increase over the past two decades. Oral squamous cell carcinoma (OSCC), which is the most common subtype of oral cavity cancer, accounts for more than 90% of oral cancer cases. The major risk factors for OSCC include smoking, alcohol misuse, smokeless tobacco use, and betel quid chewing. Despite advances in the surgical and management technologies related to OSCC, the 5-year survival rate is still approximately 50% in most countries. This mainly reflects that over 60% of patients present with stage III and IV disease, and that OSCC has a higher rate of second primary tumors than any other type of cancer. The stage at diagnosis is the key determinant of 5-year survival, with survival rates approaching 80% for patients with stage I disease but decreasing significantly for those with late-stage disease. Thus, we urgently need new approaches that will enable the early detection of OSCC.

Most cases of OSCC develop from visible lesions that are seen in the oral cavity and display oral epithelial dysplasia. Such lesions are known as oral potentially malignant disorders (OPMDs), a name that was approved by the World Health Organization (WHO) Working Group. More than 20 entities of OPMD have been recognized and reported. Lesions such as erythroplakia, submucous fibrosis, heterogeneous leukoplakia and verrucous hyperplasia have higher malignant transformation rates than others, such as thin homogeneous leukoplakia and lichen planus. The reported malignant transformation rates of OPMDs range from 0.13% to 17.5%, and vary by country. In Taiwanese patients, the overall malignant transformation of different histological types was reported to be 4.32% and the mean duration of malignant transformation was 33.56 months. In the same country, much higher transformation rates were observed for epithelial dysplasia (24.4%) and verrucous hyperplasia (20%). The malignant transformation of an OPMD to OSCC is a slow, nearly invisible process that patients may fail to notice, contributing to the delayed diagnosis of OSCC. In addition, many OPMD lesions comprise a mixture of potentially malignant cells, malignant cells that have yet to invade, malignant cells that have invaded, and normal cells. This mixture, which reflects the field-cancerization phenomenon, can cause considerable discrepancies in how different clinicians interpret the same lesion and may significantly complicate the biopsy-based diagnostic procedures. Furthermore, the fallibility of pathologists is well documented. These factors make early detection of OSCC quite challenging, and highlight the need for new approaches that can identify cancer in high-risk OPMD lesions and/or monitor the malignant transformation of such lesions.

Since the majority of OSCC cases are preceded by visible OPMDs, visual inspection of oral mucosa and pathological examination of dysplasia tissue biopsies are most often used to detect OSCC, especially in countries with a high prevalence of this disease (e.g., Taiwan). A recent study reviewed a randomized controlled trial of visual screenings for OSCC or OPMD in India (191,873 participants, with 553 OSCC and 6749 OPMD cases identified after a 15-year follow-up), and concluded that visual inspection might help reduce the death rates in patients who use tobacco and alcohol. The incidence of OSCC in Taiwan has increased over the past two decades; between 1996 and 2009, the age-standardized incidence in males reached 24.64/100,000 annually, which is among the highest in the world. Since 2010, the Taiwanese government has been promoting the Taiwan's Oral Cancer Screening Program that offers members of the at-risk population (individuals 30 years or older with habits of *betel* nut chewing or cigarette smoking) a free visual examination every other year. Each year, approximately one million participants are entitled to screening activities, including visual checkups by physicians or dentists, referrals for pathological confirmation, and subsequent treatment (Oral Cancer Screening Clinical Pathway). However, the screening results from 2011 and 2012 indicated that the screening increased the detection of early-stage (i.e., stage I) OSCC by only 3% compared to the detection rate of regular clinics (Table 1). This may not be surprising because it is challenging for first-line health workers to determine which oral lesions should be referred to a specialist for further histological confirmation. Moreover, early OSCC is largely indistinguishable from certain benign or inflammatory disorders, and multiple types of OPMD lesions may co-exist, such that the distribution of the cancerous lesion or the presence of diffusely distributed submucous fibrosis might hamper the precise capture of cancer cells via biopsy. Consequently, we urgently need a non-invasive clinical test that can be used as an effective indicator for the presence of cancer cells embedded in OPMD lesions.

TABLE 1

OSCC cases found by the visual screening program and by non-screening, regular clinics between 2011~2012 in Taiwan.

| Stage | 0-1 | 2 | 3 | 4 | Total |
|---|---|---|---|---|---|
| OSCC cases found by oral mucosal visual screening[a] | | | | | |
| Case No. | 1553 | 942 | 521 | 1605 | 4621 |
| (%) | (33.61) | (20.39) | (11.27) | (34.73) | (100) |
| OSCC cases found by non-screening, regular clinics | | | | | |
| Case No. | 1130 | 695 | 449 | 1429 | 3703 |
| (%) | (30.52) | (18.77) | (12.12) | (38.59) | (100) |

[a]1,850,697 at-risk subjects were enrolled for screening

Numerous non-invasive biomarker candidates for OSCC have been reported in recent decades. However, very few of them have been carefully evaluated and quantitatively compared in parallel using a moderate set of well-collected body-fluid samples, in an effort to identify which candidates should be subjected to further clinical validation in a large sample cohort. This may partially explain why no molecular biomarker has yet been approved by an official health agency to aid in the early detection and/or management of OSCC. In view of the foregoing, there exists in the related art a need for a novel biomarker for making a prognosis and/or diagnosis of OSCC so that the subject in need thereof could receive a suitable therapeutic regimen in time.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a method of determining whether a subject has or is at risk of developing OSCC. The method comprises the steps of, (a) obtaining a sample from the subject;

(b) determining the levels of at least two target polypeptides in the sample, wherein the at least two target polypeptides are selected from the group consisting of, annexin A2 (ANXA2), heat shock protein A5 (HSPA5), kininogen-1 (KNG1) and matrix metalloproteinase-1 (MMP1);

(c) calculating a risk score based on the levels of the at least two target polypeptides determined in the step (b); and (d) determining whether the subject has or is at risk of developing OSCC based on the risk score of the step (c).

According to some embodiments of the present disclosure, the risk score is calculated by use of logistic regression. Preferably, the risk score is calculated by the equation of, $$\text{risk score} = \frac{e^{a+b1X1+b2X2+b3X3+b4X4}}{1+e^{a+b1X1+b2X2+b3X3+b4X4}}$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1.

According to the embodiments of the present disclosure, in the step (d), when the risk score is lower than 0.4, then the subject does not have OSCC or is at low risk of developing OSCC; and when the risk score is or above 0.4, then the subject has OSCC or is at high risk of developing OSCC. For the subject having a risk score equal to or higher than 0.4, an appropriate pathological examination and/or anti-cancer treatment (e.g. a prophylactic treatment or a therapeutic treatment) may be promptly performed thereto.

In general, the subject is a mammal; preferably, a human. According to embodiments of the present disclosure, the sample is saliva.

The second aspect of the present disclosure is directed to a method of determining whether a biological sample comprises a cancerous sample. The present method comprises, (a) determining the levels of at least two target polypeptides in the biological sample, wherein the at least two target polypeptides are selected from the group consisting of, ANXA2, HSPA5, KNG1 and MMP1;

(b) calculating a risk score base on the levels of the at least two target polypeptides determined in the step (a); and (c) assessing whether the biological sample comprises cancerous oral squamous cells based on the risk score of the step (b).

According to some embodiments of the present disclosure, the risk score is calculated by use of logistic regression. Preferably, the risk score is calculated using an equation of, $$\text{risk score} = \frac{e^{a+b1X1+b2X2+b3X3+b4X4}}{1+e^{a+b1X1+b2X2+b3X3+b4X4}}$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1.

According to one embodiment of the present disclosure, when the risk score is or above 0.4, then the biological sample comprises cancerous oral squamous cells.

According to some embodiments of the present disclosure, the biological sample is saliva.

Also disclosed herein are a pharmaceutical kit and its uses in making a diagnosis or risk evaluation of OSCC. The present pharmaceutical kit comprises at least two agents useful in determining the levels of at least two target polypeptides in the subject, wherein the at least two target polypeptides are selected from the group consisting of, ANXA2, HSPA5, KNG1 and MMP1. According to one working example of the present disclosure, the at least two agents are isotope-labeled polypeptides comprising the amino acid sequences independently selected from the group consisting of SEQ ID NOs: 5, 6, 7 and 8.

Based on the quantified result, a risk score can be generated and serves as an indicator of OSCC. According to embodiments of the present disclosure, when the risk score is lower than 0.4, then the subject does not have OSCC or is at low risk of developing OSCC; and when the risk score is or above 0.4, then the subject has OSCC or is at high risk of developing OSCC.

Exemplary assays suitable to determine the levels of at least two target polypeptides include, but are not limited to, enzyme-linked immunosorbent assay (ELISA), strip-based rapid test, western blotting, mass spectrometry, protein microarray, flow cytometry, immunofluorescence, immunohistochemistry, and multiplex detection assay. In one specific example of the present disclosure, the levels of at least two target polypeptides is determined by liquid chromatography-tandem mass spectrometry with multiple reaction monitoring (MRM) mode (LC-MRM-MS).

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DETAILED DESCRIPTION OF THE INVENTION

Figure 1A:
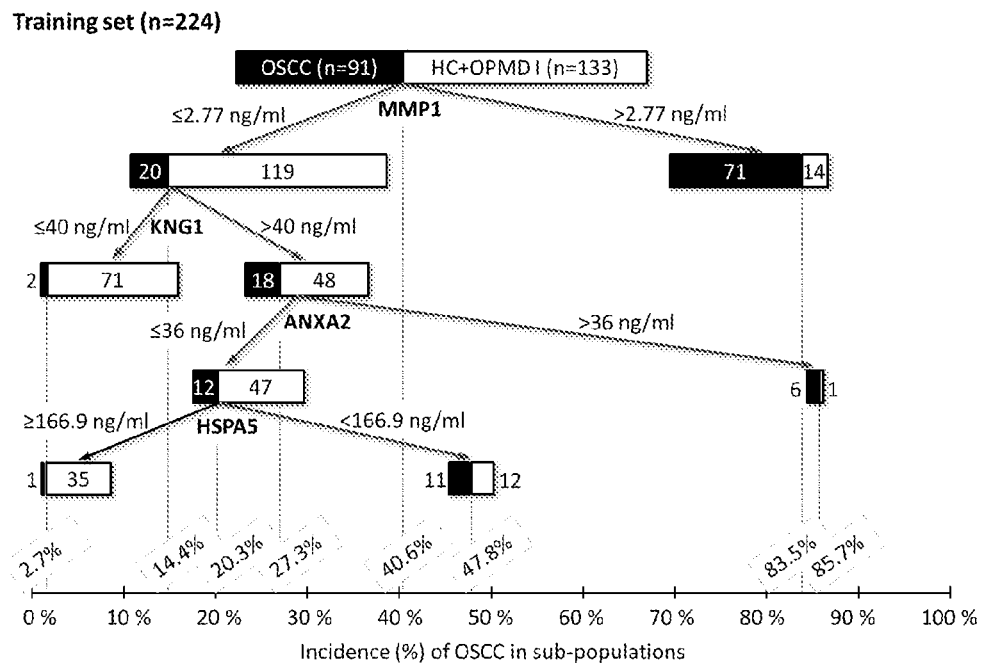
FIG. 1A illustrates the classification tree depicting the selected four proteins and its cut-off value of concentration (ng/ml) at each split node.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

"Percentage (%) amino acid sequence identity" with respect to the polypeptide sequences identified herein is defined as the percentage of polypeptide residues in a candidate sequence that are identical with the amino acid residues in the specific polypeptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two polypeptide sequences was carried out by computer program Blastp (protein-protein BLAST) provided online by Nation Center for Biotechnology Information (NCBI). The percentage amino acid sequence identity of a given polypeptide sequence A to a given polypeptide sequence B (which can alternatively be phrased as a given polypeptide sequence A that has a certain % amino acid sequence identity to a given polypeptide sequence B) is calculated by the formula as follows:

$$\frac{X}{Y} \times 100\%$$

where X is the number of amino acid residues scored as identical matches by the sequence alignment program BLAST in that program's alignment of A and B, and where Y is the total number of amino acid residues in A or B, whichever is shorter.

The term "receiver operating characteristic (ROC) curve" as used herein refers to a plot of the true positive rate against the false positive rate for determining a possible cut-off point of a prognostic or diagnostic test. A ROC consists of graphing (1-specificity) on the x-axis vs. the sensitivity values on the y-axis. A high sensitivity results in low number of false negative cases. A high specificity refers to low number of false positive cases. The term "cut-off point" refers to a number obtained from an ROC representing a balance between sensitivity and specificity of the prognostic or diagnostic test. A cut-off range can encompass a number of cut-off embodiments, where each represents a different balance between sensitivity and specificity.

The term "area under the curve (AUC)" is used in its art accepted manner and is defined as the area under the ROC curve. An AUC ranging between 0.5-1.0 is a measure for the accuracy of a prognostic or diagnostic test, in which the higher the AUC value, the better the performance of the prognostic or diagnostic test. The AUC value is often presented along with its 95% confidence interval (CI) that refers to a statistical range with a specified probability that a given parameter lies within the range.

Throughout the present disclosure, the term "assessing" refers to a process in which the health status of a subject is determined. The health status of the subject may indicate a diagnosis, prognosis, or increased risk of a cancer in said subject.

The term "risk" herein refers to the potential that a result will lead to an undesirable outcome i.e., occurrence, progression or recurrence of OSCC. A subject may be classified as "high risk" or "low risk" according to the data obtained from said subject, sample or event. As to the risk score described in the present disclosure, the patient with a risk score≥0.4 is classified as "high risk", which indicates that he/she have a higher probability of developing HCC within about five years than the other subjects investigated. The patient with a risk score<0.4 is classified as "low risk", which indicates that he/she have a lower probability of developing HCC within about five years than the other subjects investigated.

As used herein, the term "prophylactic treatment" or "preventive treatment" are interchangeable, and refers to either preventing or inhibiting the development of a clinical condition or disorder or delaying the onset of a pre-clinically evident stage of a clinical condition or disorder; for example, OSCC. According to embodiments of the present disclosure, the term "prophylactic treatment" refers to a preventative treatment for a subject predisposed to OSCC. In general, the predisposition may be due to genetic factors, age, sex, injury, and the like.

As used herein, the term "therapeutic treatment" refers to administering treatment to a subject already suffering from a disease (e.g., OSCC) thus causing a therapeutically beneficial effect, such as ameliorating existing symptoms, ameliorating the underlying metabolic causes of symptoms, postponing or preventing the forther development of a disorder and/or reducing the severity of symptoms that will or are expected to develop.

The term "subject" refers to an animal including the human species that is evaluable with the method of the present disclosure. The term "subject" is intended to refer to both the male and female gender unless one gender is specifically indicated, and may be any age, e.g., a child or adult.

The first aspect of the present disclosure is directed to a method for determining whether a subject has or is at risk of developing OSCC. According to embodiments of the present disclosure, the method comprises the steps of, (a) obtaining a sample from the subject;
(b) determining the levels of at least two target polypeptides in the sample, wherein the at least two target polypeptides are selected from the group consisting of, ANXA2, HSPA5, KNG1 and MMP1;
(c) calculating a risk score based on the levels of the at least two target polypeptides determined in the step (b); and
(d) determining whether the subject has or is at risk of developing OSCC based on the risk score of the step (c).

In the step (a), a sample is obtained from the subject. The subject is a mammal; preferably, a human. According to the preferred example of the present disclosure, the subject is an Asian. In one working example of the present disclosure, the subject is a Chinese. According to the embodiment of the present disclosure, the sample is preferably saliva.

In the step (b), the levels of at least two of ANXA2, HSPA5, KNG1 and MMP1 (e.g., any two, three or four of ANXA2, HSPA5, KNG1 and MMP1) in the sample are determined. According to some embodiments of the present disclosure, two of ANXA2, HSPA5, KNG1 and MMP1 are quantified (either as relative values or absolute values) so as to produce a two-marker panel useful in making a diagnosis or a prognosis of the cancer. Such a two-marker panel may consist of, (1) ANXA2 and HSPA5 polypeptides, (2) ANXA2 and KNG1 polypeptides, (3) ANXA2 and MMP1 polypeptides, (4) HSPA5 and KNG1 polypeptides, (5) HSPA5 and MMP1 polypeptides, or (6) KNG1 and MMP1 polypeptides. According to certain embodiments of the present disclosure, three of ANXA2, HSPA5, KNG1 and MMP1 are quantified (either as relative values or absolute values) so as to produce a three-marker panel useful in making a diagnosis or a prognosis of the cancer. Such a three-marker panel may consist of, (1) ANXA2, HSPA5 and KNG1, (2) ANXA2, HSPA5 and MMP1, (3) ANXA2, KNG1 and MMP1, or (4) HSPA5, KNG1 and MMP1. According to other embodiments of the present disclosure, all ANXA2, HSPA5, KNG1 and MMP1 are quantified (either as relative values or absolute values) so that a four-marker panel is produced.

In general, the levels of ANXA2, HSPA5, KNG1 and/or MMP1 can be determined by any assay familiar with the skilled artisan; for example, ELISA, strip-based rapid test, western blotting, mass spectrometry, protein microarray, flow cytometry, immunofluorescence, immunohistochemistry, and multiplex detection assay. According to one embodiment of the present disclosure, the levels of ANXA2, HSPA5, KNG1 and/or MMP1 is determined by liquid chromatography-tandem mass spectrometry with multiple reaction monitoring (MRM) mode (LC-MRM-MS), an assay widely used in the field of proteomics that provides a specific and precise means to quantify polypeptides.

According to some embodiments of the present disclosure, the target polypeptide ANXA2 comprises the amino acid sequence at least 90% (i.e., 90%, 91%, 92&, 93%, 94%, 95%, 96%, 97%, 98%, 99% or 100%) identical to SEQ ID NO: 1; the target polypeptide HSPA5 comprises the amino acid sequence at least 90% identical to SEQ ID NO: 2; the target polypeptide KNG1 comprises the amino acid sequence at least 90% identical to SEQ ID NO: 3; and the target polypeptide MMP1 comprises the amino acid sequence at least 90% identical to SEQ ID NO: 4. According to the working example of the present disclosure, the target polypeptide ANXA2 has the amino acid sequence of SEQ ID NO: 1; the target polypeptide HSPA5 has the amino acid sequence of SEQ ID NO: 2; the target polypeptide KNG1 has the amino acid sequence of SEQ ID NO: 3; and the target polypeptide MMP1 has the amino acid sequence of SEQ ID NO: 4.

In the step (c), the two-, three- or four-marker panel quantified in the step (b) are used to calculate the predictive probability as a risk score. According to some embodiments of the present disclosure, the logistic regression is used to analyze the two-, three- or four-marker panel in the purpose of calculating the risk score. According to preferred embodiments of the present disclosure, the risk score is calculated using an equation of, $$\text{risk score} = \frac{e^{a+b1X1+b2X2+b3X3+b4X4}}{1+e^{a+b1X1+b2X2+b3X3+b4X4}}$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1.

According to one working example of the present disclosure, the constant value and the coefficient of variation may vary with the marker panel, and the risk score established by specified target polypeptides is calculated in accordance with the equations listed in Tables 12-13 or Tables 16-17.

According to one embodiment of the present disclosure, the risk score is calculated based on the analysis of two-marker panel, which comprises two target polypeptides selected from the group consisting of, ANXA2, HSPA5, KNG1 and MMP1. According to another embodiment of the present disclosure, the risk score is calculated based on the analysis of three-marker panel, which comprises three target polypeptides selected from the group consisting of, ANXA2, HSPA5, KNG1 and MMP1. According the preferred embodiment of the present disclosure, the risk score is calculated based on the analysis of four-marker panel, which comprises four target polypeptides, including ANXA2, HSPA5, KNG1 and MMP1.

In the step (d), the risk score calculated in the step (c) is used to assess whether the subject has or is at risk of developing OSCC. According to some embodiments of the present disclosure, the risk score is useful in distinguishing non-OSCC subject (e.g., healthy subject or oral potentially malignant disorder (OPMD) patients) from OSCC patients. In these embodiments, the risk score equal to or higher than 0.4 ($\geq 0.4$) indicates that the subject has OSCC (positive predictive value (PPV) was 75.5%-89.1%; instead, the risk score lower than 0.4 (<0.4) indicates that the subject does not have OSCC (negative predictive value (NPV) was 81.9%-93.6%); the accuracy for discriminating non-OSCC subject and OSCC patients was 80.9%-86.7%. According to one working example, the risk score is correlated with the stage of OSCC, in which the patient having early stage of OSCC has lower risk score as compared to the patient having advanced stage of OSCC. According to other embodiments of the present disclosure, the risk score is useful in making a risk evaluation of OSCC occurrence in an OPMD (such as OPMD I or OPMD II) patient. In these embodiments, when the risk score is equal to or higher than 0.4 ($\geq 0.4$), then the patient is at high risk of developing OSCC (transforming rate=37.8%); alternatively, when the risk score is lower than 0.4 (<0.4), then the patient is at low risk of developing OSCC (transforming rate=7.8%).

The clinical practitioner may make a prompt diagnosis and treatment to the subject in need thereof in accordance with the present risk score derived from the present method, in which the subject having a risk score equal to or higher than 0.4 shall be subjected to an anti-cancer treatment (e.g., a prophylactic treatment or a therapeutic treatment) or be placed in an intensive follow-up regimen.

The second aspect of the present disclosure is thus directed to a method of diagnosing and treating OSCC in a subject. The method comprises determining whether or not a subject has OSCC by the steps (a) to (c) of the aforementioned method followed by administering to the subject having a risk score equal to or higher than 0.4 an effective amount of an anti-cancer treatment. In general, the anti-cancer treatment can be a preventive treatment (e.g., administration of anti-oxidant agents), a therapeutic treatment (e.g., chemotherapy, surgical resection, radiation therapy and immunotherapy) or the combination thereof. Preferably, the anti-cancer treatment is surgical resection of OSCC.

The third aspect of the present disclosure pertains to a method of determining whether a biological sample is a cancerous sample. The present method comprises, (a) determining the levels of at least two target polypeptides in the biological sample, wherein the at least two target polypeptides are selected from the group consisting of, ANXA2, HSPA5, KNG1 and MMP1;

(b) calculating a risk score based on the levels of the at least two target polypeptides determined in the step (a); and (c) assessing whether the biological sample is the cancerous sample based on the risk score of the step (b).

The steps (a) to (b) of the method for assessing the biological sample (i.e., the method of the third aspect) are respectively the same as the steps (b) to (c) of the method for assessing the sample obtained from the subject (i.e., the method of the first aspect) discussed hereinabove, and hence, detailed description thereof is omitted herein for the sake of brevity.

In the step (c), the biological sample is evaluated by the risk score calculated in the step (b). According to one embodiment of the present disclosure, the cancerous sample is an OSCC sample; in the embodiment, the risk score of the biological sample is equal to or higher than 0.6. According to another embodiment of the present disclosure, the cancerous sample comprises cancerous oral squamous cells, for example, an sample isolated from OPMS II patient, in which the cancerous cell are present in the sample but not detected by conventional methods (e.g., biopsy) or the abnormal lesions potentially developed to cancer in the future (<5 years); in the embodiment, the risk score of the biological sample is equal to or higher than 0.4, but lower than 0.6.

According to some embodiments of the present disclosure, the biological sample is saliva.

Also disclosed herein is a pharmaceutical kit for determining whether a subject has or is at risk of developing OSCC. The present pharmaceutical kit comprises at least two agents (e.g., two, three or four agents) useful for determining the levels of at least two of ANXA2, HSPA5, KNG1 and MMP1 (e.g., any two, three or four of ANXA2, HSPA5, KNG1 and MMP1) in the subject. For example, the present pharmaceutical kit may comprise two agents respectively useful for quantifying the levels of any two of ANXA2, HSPA5, KNG1 and MMP1. Alternatively, the present pharmaceutical kit may comprise three agents respectively useful for quantifying the levels of any three of ANXA2, HSPA5, KNG1 and MMP1. Optionally, the present pharmaceutical kit may comprise four agents respectively useful for quantifying the levels of ANXA2, HSPA5, KNG1 and MMP1.

Depending on the desired purpose, each of the agents may be a polypeptide (e.g., an antibody or an isotope-labeled polypeptide) or an aptamer. According to one working example of the present disclosure, each of the agents is an isotope-labeled polypeptide, in which the agents for quantifying ANXA2 (SEQ ID NO: 1), HSPA5 (SEQ ID NO: 2), KNG1 (SEQ ID NO: 3) and MMP1 (SEQ ID NO: 4) respectively comprise the amino acid sequences of SEQ ID NOs: 5, 6, 7 and 8.

The assay for determining the levels of ANXA2, HSPA5, KNG1 and/or MMP1 may vary with the type of agents. According to one embodiment of the present disclosure, each of the agents is an isotope-labeled polypeptide, and each of the ANXA2, HSPA5, KNG1 and/or MMP1 is quantified by LC-MRM-MS.

The quantified values of ANXA2, HSPA5, KNG1 and/or MMP1 are then used to calculate a risk score so as to make a diagnosis or risk evaluation of OSCC. As mentioned above, the risk score may be calculated by use of logistic regression; preferably, by the equation of, $$\text{risk score} = \frac{e^{a+b1X1+b2X2+b3X3+b4X4}}{1 + e^{a+b1X1+b2X2+b3X3+b4X4}}$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1.

According to one working example of the present disclosure, the constant value and the coefficient of variation may vary with the marker panel, and the risk score established by specified target polypeptides is calculated in accordance with the equations listed in Tables 12-13 or Tables 16-17.

According to embodiments of the present disclosure, when the risk score is lower than 0.4, then the subject does not have OSCC or is at low risk of developing OSCC; and when the risk score is or above 0.4, then the subject has OSCC or is at high risk of developing OSCC.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods

Samples

Prior to the pre-treatment collection of saliva samples, each subject signed an informed consent form approved by the Institutional Review Board of Chi-Mei Medical Center, permitting the use of saliva samples for the present invention. Saliva samples were collected from 96 healthy controls (normal mucosa), 103 individuals with low-risk OPMDs (OPMD I), 130 individuals with high-risk OPMDs (OPMD II), and 131 patients with OSCC. The samples were obtained at Chi-Mei Medical Center (Liouying, Taiwan) from 2008 to 2013 (Table 2). All subjects were enrolled in the Taiwan's Oral Cancer Screening Program. The diagnoses of OSCC were confirmed by biopsy, and patients underwent routine checkups according to the standard protocol. The OPMD cases were classified according to previous publications. The 130 cases of OPMD II were divided into nine categories: erythroleukoplakia (n=6, 4.6%), erythroplakia plus high-grade oral submucous fibrosis (OSF) (n=1, 0.8%), heterogeneous leukoplakia (n=5, 3.8%), leukoplakia plus high-grade OSF (n=7, 5.4%), high-grade OSF (n=21, 16.2%), speckle leukoplakia (n=7, 5.4%), verrucous leukoplakia (n=1, 0.8%), verrucous hyperplasia (n=44, 33.8%), and verrucous hyperplasia plus OSF (n=38, 29.2%). The 103 cases of OPMD I were distributed to three categories: leukoplakia (n=91, 88.3%), lichenoid lesions (n=4, 3.9%), and low-grade OSF (n=8, 7.8%).

TABLE 2

Demographic characteristics and use of cigarettes and betel nuts by the enrolled subjects.

|  | Control | OPMD I | OPMD II | OSCC | p* | Total |
|---|---|---|---|---|---|---|
| Case no. | 96 (20.9%) | 103 (22.4%) | 130 (28.3%) | 131 (28.5%) |  | 460 (100.0%) |
| Sex |  |  |  |  |  |  |
| Male | 96 (100.0%) | 102 (99.0%) | 129 (99.2%) | 129 (98.5%) | 0.6763[1] | 456 (99.1%) |
| Femal | 0 (0.0%) | 1 (1.0%) | 1 (0.8%) | 2 (1.5%) |  | 4 (0.9%) |
| Age | 48.75 ± 11.84 | 49.49 ± 10.71 | 51.36 ± 10.51 | 52.51 ± 9.65 | 0.0320[2] | 50.72 ± 10.68 |
| Smoke (packs per day × years) | 19.13 ± 11.15 | 24.59 ± 24.15 | 31.03 ± 21.48 | 27.01 ± 22.39 | 0.0030[2] | 25.96 ± 21.09 |
| Betel nut (nuts per day × years) | 138.06 ± 328.63 | 172.18 ± 187.91 | 389.63 ± 524.15 | 386.89 ± 477.71 | <.0001[2] | 287.66 ± 430.67 |

[1]Fisher's exact test
[2]Analysis of variance (ANOVA)
p-value of interset

The saliva samples were collected and processed as described previously. Briefly, during oral mucosal examination, unstimulated whole saliva was collected. The donors avoided eating, drinking, smoking, and using oral hygiene products for at least 1 hour prior to collection. Each sample was centrifuged at 3000×g for 15 minutes at 4° C. The supernatant was treated with a protease inhibitor cocktail (Sigma, St. Louis, Mo., USA), and aliquots were stored at −80° C.

Selection of Surrogate Peptides for Target Proteins

One surrogate tryptic peptide was selected for each target protein. First, we chose peptides that were detected in our previously reported shotgun MS datasets representing the secretomes of cancer cell lines and primary cells and the tissue proteomes of OSCC. We then further selected: (a) unique peptides containing eight to 23 residues without any known post-translational modification site, which determined from the human protein reference database, and no sequential or missed trypsin cleavage site; (b) peptides without chemically reactive amino acids, such as Cys or Met; (c) peptides without sequences potentially leading to missed cleavage, such as RP or KP; and (d) peptides with a high identification score in the MS2 data. Peptides that fit all these criteria were further analyzed using the MRMPilot software (version 2.1; AB Sciex, Forster City, Calif., USA) to predict whether their fragment ions would be suitable for detection by MS. In the case of four target proteins (DSG3, HGF, CRNN, and TP53) for which no empirical evidence was available or no suitable peptide was found in the shotgun MS datasets, we obtained all possible tryptic peptides by in silico prediction and selected their surrogate peptides using the above-described criteria.

Tryptic Digestion and Addition of Stable Isotope-Labeled Standard (SIS) Peptides Each saliva sample was analyzed by LC-MRM-MS three times using the three processed replicates. The protein concentration of each saliva sample was measured using a BCA Protein Assay Kit (Thermo Scientific Pierce, USA). 15 μg of salivary proteins were dissolved in 15 μl of 25 mM ammonium bicarbonate, and then denatured with 15 µl of 10% sodium deoxycholate (DOC). The sample was then diluted with 81.35 µl of 25 mM ammonium bicarbonate, reduced by incubation with 12.4 µl of 50 mM Tris (2-carboxyethyl) phosphine (TCEP) at 60° C. for 30 minutes, and alkylated by incubation with 13.75 µL of 100 mM iodoacetamide at 37° C. for 30 minutes. Modified sequencing-grade trypsin (Promega, Madison, Wis.) was added to the reduced and alkylated samples at a 20:1 protein/enzyme ratio, and the samples were digested at 37° C. for 9 hours. The tryptic digestion was stopped, and the samples were stored at −20° C. until further processing. Each sample was spiked with a 49 SIS peptide standard cocktail (see below) and acidified with 6 µl of 10% formic acid and 1.5 µl of 10% trifluoroacetic acid (TFA) to precipitate DOC. For spiking, digests were mixed with an equivalent amount of an SIS mixture containing 49 [$^{13}C_6$; $^{15}N_2$]Lys or [$^{13}C_6$; $^{15}N_4$]Arg-coded SIS peptides. The SIS peptides were synthesized and purified at the UVic-Genome BC Proteomics Centre, BC Canada. The purities of SIS for ANXA2, HSPA5, KNG1 and MMP1 are respectively 93.4%, 98.3%, 98.2% and 99.1%. The sequences and concentrations of SIS peptides for specified target polypeptides are illustrated in Table 3, in which the SIS peptides for ANXA2, HSPA5, KNG1 and MMP1 respectively have the sequences of "QDIAFAYQR" (SEQ ID NO: 5), "ITPSYVAFTPEGER" (SEQ ID NO: 6), "TVGSDTFYSFK" (SEQ ID NO: 7) and "DIYSSFGFPR" (SEQ ID NO: 8). In the SIS heavy peptides, the Carcon-12 ($^{12}C$) of Arginine (R) and Lysine (K) was replaced by Carcon-13 ($^{13}C$), and the Nitrogen-14 ($^{14}N$) of Arginine (R) and Lysine (K) was replaced by Nitrogen-15 ($^{15}N$). The acidified samples were centrifuged at room temperature for 2 minutes at 16,000×g to remove DOC, and each supernatant was stored at −20° C. for subsequent processing. At that point, the sample was desalted and concentrated by solid phase extraction with a Waters Oasis HLB µElution Plate (Waters, Mass.) using the manufacturer's recommended procedure with some modification. Briefly, the resin was rinsed with acetonitrile and equilibrated with equilibration buffer (0.1% TFA and 0.1% formic acid). The salivary protein digest was loaded, washed with water, and eluted by two applications of 50 µl of 70% acetonitrile. The eluted samples were frozen, dried by lyophilization, and then rehydrated with 0.1% formic acid (v/v) to a working concentration of 0.25 µg/µl for LC-MRM-MS analysis.

LC-MRM-MS Analysis and Data Acquisition

A nanoACQUITY UPLC System (Waters, USA) was used for the injection of salivary peptides. The LC-MRM/MS analysis (see below) of each sample took 70 minutes. Fourmicroliter samples (representing 1 µg of peptides) were injected onto a resolving analytical column (nanoACQUITY UPLC C18, 150 µm×10 mm, 1.7-µm particle size; Waters) at a flow rate of 1 µl/min in 97% buffer A (0.1% formic acid in $H_2O$) (J.T. Baker, USA) and 3% buffer B (0.1% formic acid in acetonitrile) (J.T. Baker) for 10 minutes. The samples were then separated at a flow rate of 400 nl/min with a 48-minute linear gradient from 3% to 28% buffer B, a 5-minute linear gradient from 28% to 38% buffer B, and a final 1-minute linear gradient from 38% to 95% buffer B. The analytical column was then reconditioned by holding buffer B at 95% for 5 minutes, ramping back down to 3% solvent B over 1 minute, and re-equilibrating for 10 minutes with 3% buffer B. A blank solvent injection (25-minute analysis at 400 nl/min) was run between each sample to prevent sample carryover on the UPLC column.

An AB/MDS Sciex 5500 QTRAP with a nano-electrospray ionization source controlled by the Analyst 1.5.1 software (all from AB Sciex, Singapore) was used for all LC-MRM-MS analyses. Acquisition was performed using the following parameters: ion spray voltage, 1900-2200 V; curtain gas setting, 20 psi (UHP nitrogen); interface heater temperature, 150° C.; MS operating pressure, $3.5 \times 10^{-5}$ Torr; Q1 and Q3, unit resolution (0.6-0.8 Da full width at half height). The MRM acquisition conducted using three MRM ion pairs per peptide with the following constraints: fragment-ion-specific-tuned declustering potential (DP); entrance potential (EP); collision energy (CE); collision cell exit potential (CXP); and retention time. A scheduled MRM option was used for all data acquisition, with a target cycle time of 1 second and a 4-minute MRM detection window. The transitions of the 49 tested peptides (corresponding to 49 target proteins) were quantified in an LC-MRM-MS run. The MRM parameters of the target polypeptides ANXA2, HSPA5, KNG1 and MMP1 were summarized in Table 3.

TABLE 3

MRM parameters for quantifying target polypeptides

| Protein | Fixed SIS Peptide Concentration (fmol/ug total protein) | Peptide | Q1/Q3 Mass (Da) | Q3 type |
|---|---|---|---|---|
| ANXA2 | 5 | QDIAFAYQR (SEQ ID NO: 5).1.light | 556.28/537.28 | 2/y4 |
| | | QDIAFAYQR (SEQ ID NO: 5).2.light | 556.28/684.35 | 2/y5 |
| | | QDIAFAYQR (SEQ ID NO: 5).3.light | 556.28/755.38 | 2/y6 |
| | | QDIAFAYQR (SEQ ID NO: 5).1.heavy | 561.28/547.29 | 2/y4 |
| | | QDIAFAYQR (SEQ ID NO: 5).2.heavy | 561.28/694.35 | 2/y5 |
| | | QDIAFAYQR (SEQ ID NO: 5).3.heavy | 561.28/765.39 | 2/y6 |
| HSPA5 | 5 | ITPSYVAFTPEGER (SEQ ID NO: 6).1.light | 783.89/676.81 | 2/y12(2+) |
| | | ITPSYVAFTPEGER (SEQ ID NO: 6).2.light | 783.89/906.43 | 2/y8 |
| | | ITPSYVAFTPEGER (SEQ ID NO: 6).3.light | 783.89/835.39 | 2/y7 |
| | | ITPSYVAFTPEGER (SEQ ID NO: 6).1.heavy | 788.9/681.83 | 2/y12(2+) |
| | | ITPSYVAFTPEGER (SEQ ID NO: 6).2.heavy | 788.9/916.44 | 2/y8 |
| | | ITPSYVAFTPEGER (SEQ ID NO: 6).3.heavy | 788.9/845.4 | 2/y7 |
| KNG1 | 5 | TVGSDTFYSFK (SEQ ID NO: 7).1.light | 626.3/1051.47 | 2/y9 |
| | | TVGSDTFYSFK (SEQ ID NO: 7).2.light | 626.3/792.39 | 2/y6 |
| | | TVGSDTFYSFK (SEQ ID NO: 7).3.light | 626.3/907.42 | 2/y7 |
| | | TVGSDTFYSFK (SEQ ID NO: 7).1.heavy | 630.31/1059.49 | 2/y9 |
| | | TVGSDTFYSFK (SEQ ID NO: 7).2.heavy | 630.31/800.41 | 2/y6 |
| | | TVGSDTFYSFK (SEQ ID NO: 7).3.heavy | 630.31/915.43 | 2/y7 |

TABLE 3-continued

MRM parameters for quantifying target polypeptides

| Protein | Fixed SIS Peptide Concentration (fmol/ug total protein) | Peptide | Q1/Q3 Mass (Da) | Q3 type |
|---|---|---|---|---|
| MMP1 | 10 | DIYSSFGFPR (SEQ ID NO: 8).1.light | 594.79/797.39 | 2/y7 |
|  |  | DIYSSFGFPR (SEQ ID NO: 8).2.light | 594.79/960.46 | 2/y8 |
|  |  | DIYSSFGFPR (SEQ ID NO: 8).3.light | 594.79/476.26 | 2/y4 |
|  |  | DIYSSFGFPR (SEQ ID NO: 8).1.heavy | 599.79/807.4 | 2/y7 |
|  |  | DIYSSFGFPR (SEQ ID NO: 8).2.heavy | 599.79/970.47 | 2/y8 |
|  |  | DIYSSFGFPR (SEQ ID NO: 8).3.heavy | 599.79/486.27 | 2/y4 |

The Carcon-12 ($^{12}C$) and Nitrogen-14 ($^{14}N$) of the underlined arginine (R) and lysine (K) residues are respectively replaced by Carcon-13 ($^{13}C$) and Nitrogen-15 ($^{15}N$).

MRM Data Analysis and Generation of Calibration Curves

All MRM data were processed using the MultiQuant software (version 2.1; AB Sciex) with the MQ4 algorithm utilized for peak integration. For data acquisition, scheduled MRM was used to reduce cycle times and generate more points per peak, thus ensuring more accurate quantitation. A standard curve was generated for each target peptide, using different amounts of a tryptic digest from a standard saliva sample. This standard was prepared by pooling the saliva from three individuals (two OSCC patients and one control individual) and subjecting the pooled saliva to tryptic digestion, as described for the clinical samples. This standard saliva sample was then spiked with a constant level of SIS peptides, and used to generate an 11-point (blank, and A to J) dilution curve in which the SIS peptide concentration was held constant and the light peptide concentration was varied by appropriate dilution of the tryptic digest. A fixed amount of the 49-SIS-peptide cocktail was added to each of the clinical saliva samples. The composition of the SIS cocktail was adjusted according to the concentration levels and signal intensities of the endogenous salivary peptides, to ensure the accuracy of the quantitation. The standard saliva sample (sample I) was added at the same concentration as the unknown (1 µg endogenous peptides injected), while samples A, B, C, D, E, F, G, H, and J corresponded to 0.00001-, 0.0001-, 0.005-, 0.01-, 0.05, 0.1-, 0.2-, 0.5- and 2 times the concentration of the standard sample (sample I). A fixed amount of the 49 SIS cocktail was spiked into samples A to I, whereas a 0.5-fold dilution of the SIS cocktail was added to sample J. The accurate concentration of each SIS peptide was known, allowing the concentration of the protein in the unknown sample to be determined from the observed peak area ratios.

Three independent technical repeats were performed (from digestion to the final LC-MRMMS step) for each saliva sample and concentration point on the calibration curves. Linear regression of all calibration curves was performed using a standard 1/x (x=concentration ratio) weighting option, which assisted in covering a wide dynamic range. Three MRM ion pairs were measured per peptide; one was used as the quantifier, while the other two were used to verify the retention times and reveal any signal interference. All integrated peaks were manually inspected to ensure correct peak detection and accurate integration. For the statistical analysis, the concentration values of proteins without detectable peaks were assigned as zero. The concentration of each target protein is calculated as the mean of the measured concentrations from the three independent experiments and expressed in fmol/µg and ng/ml of salivary protein; this was derived from the determined molar level of each prototypic peptide, assuming complete tryptic digestion and 100% peptide recovery.

Statistical Analyses

Categorical and continuous data were compared among the four groups (healthy control, OPMD I, OPMD II, and OSCC) using Fisher's exact test, one-way analysis of variance (ANOVA), and/or the nonparametric Mann-Whitney test, where appropriate. In cases where the ANOVA results were significant, Student-Newman-Keuls post-hoc multiple comparisons were used to identify the means that differed. Test performance was assessed by generating the receiver operating characteristic (ROC) curve, the area under the ROC curve (AUC), the positive likelihood ratio (LR+) and the negative likelihood ratio (LR−) for each biomarker or combination of biomarkers in the screening of OSCC. The optimal cutoff values were determined by the highest Youden index (defined as Se+Sp-1) obtained from an ROC curve fitted with a smooth nonparametric method to reduce data-driven selection bias.

For generating biomarker panels, we applied three statistical methods commonly used to distinguish between non-disease and disease states: k-nearest neighbors discrimination, logistic regression, and classification and regression trees (CART). CART comprised two steps, tree construction and tree pruning, and fitting was performed by binary recursive partitioning. During tree construction, when the program reached a splitting node, it repeatedly chose an appropriate splitting point for each possible predictor until the minimum cost of misclassification was reached. The samples were randomly divided at a ratio of 2:1, which was adjusted similar demographic characteristics, by Hold-Out method. The simulation was repeated 1000 times by Bootstrap method, the best tree size and the most import predictors in the training set (n=224) were chosen, and the final tree model was validated in an independent test set (n=106). After the tree was constructed, the continuous value of selected markers (numerical variables) were dichotomized into binary variables based on its cut-off concentration of splitting point. Where positive prediction to OSCC was assigned as 1 when concentration level was higher than the cut-off value in ANXA2, KNG1, and MMP1, or lower than the cut-off value in HSPA5, otherwise negative prediction was assigned as 0. The binary variables generated by CART for the selected markers were included as covariates in a logistic regression to obtain the predicted probability of having OSCC, using the equation of, $$\text{risk score} = \frac{e^{a+b1X1+b2X2+b3X3+b4X4}}{1+e^{a+b1X1+b2X2+b3X3+b4X4}},$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1. Discrimination and logistic regression were performed using SAS, and CART was performed using the R (v3.0.3) statistical package, rpart.

Example 1 Generation of Candidate Biomarker Panels 1.1 Selection of Biomarker for Detecting OSCC The biomarker associated with OSCC was selected from a training set (n=224) and validated with a test set (n=106); the sets were generated from the 330 subjects in the OSCC (n=131) and non-OSCC (n=199) groups, using random division at a ratio of 2:1 and adjustment to obtain similar demographic characteristics (data not known). All the data were analyzed by logistic regression, discriminant analysis, and classification and regression tree (CART) analysis (Table 4). Four target proteins were selected by CART analysis as the biomarker panel for the detection of OSCC, including ANXA2, HSPA5, KNG1 and MMP1 (FIG. 1A). MMP1 was used as the first biomarker; it was the most likely to distinguish OSCC from non-OSCC individuals using a cutoff of 2.77 ng/mL, which correctly identified 71 of 91 OSCC cases (78%) while yielding 14 false positives. Subjects with salivary MMP1 lower than 2.77 ng/mL (n=139) were then filtered for those with salivary KNG1>40 ng/mL and ANXA2>36 ng/mL; this analysis correctly identified six of the remaining 20 OSCC cases while yielding one false positive. Finally, subjects with salivary KNG1>40 ng/mL but ANXA2<36 ng/mL (n=59) were filtered for those with HSPA5<166.9 ng/mL; this analysis correctly identified 11 OSCC subjects. Thus, the algorithm correctly identified 88 of 91 OSSC samples and 106 of 133 non-OSCC samples in the training set, for a sensitivity of 96.7% and a specificity of 79.7%. In the test set, this four-protein panel yielded a sensitivity of 87.5% and a specificity of 78.8% for detecting OSCC. The accuracies in the training and test sets were 86.6% and 82.1%, respectively (Table 4).

TABLE 4

Comparison of the three statistical methods used to establish the marker panel.

| Markers | CART ANXA2, HSPA5, KNG1, MMP1 | Logistic regression[#] ANXA2, HSPA5, KNG1, PRDX2 | Discriminant ANXA2, FLNA, HSPA5, KNG1, PRDX2, TIMP1 |
|---|---|---|---|
| Training set (n = 224) | | | |
| Accuracy | 86.61% | 83.50% | 78.10% |
| Sensitivity | 96.70% | 75.80% | 51.60% |
| Specificity | 79.70% | 88.70% | 96.20% |
| LR[+] | 4.76 | 6.70 | 13.60 |
| LR[−] | 0.04 | 0.30 | 0.50 |
| Test set (n = 106) | | | |
| Accuracy | 82.08% | 85.80% | 78.30% |
| Sensitivity | 87.50% | 85.00% | 57.50% |
| Specificity | 78.79% | 86.40% | 90.90% |
| LR[+] | 4.13 | 6.20 | 6.30 |
| LR[−] | 0.16 | 0.20 | 0.50 |

[#]Probability >0.4

As smoking and betel nut chewing are two of the most important risk factors for the development of OSCC, a correlation analysis was used to evaluate the relationship between age/smoking/betel nut chewing and the four protein markers. However, there was no significant association between the levels of these four proteins and the risk habits of the 460 subjects (Table 5). Thus, compared to visual examination-based oral cancer screening, which reportedly showed a uniformly high specificity (~98%) but varied sensitivity (50%-99%) in different countries, our CART-selected four-protein panel appears to be more suitable for the detection of OSCC cases enrolled in the Taiwan's Oral Cancer Screening Program.

TABLE 5

Correlation analysis of the salivary levels of the four biomarkers and smoking or betel nut chewing among the 460 subjects.

| | | Age | Smoke | Betel | 19_MMP1 | 1_ANXA2 | 16_KNG1 | 13_HSPA5 |
|---|---|---|---|---|---|---|---|---|
| Age | Pearson's | 1 | 0.21845 | 0.08635 | −0.00535 | 0.08459 | 0.11626 | 0.13663 |
| | rp | | <.0001 | 0.0643 | 0.9089 | 0.0699 | 0.0126 | 0.0033 |
| Smoke | Pearson's | 0.21845 | 1 | 0.27922 | 0.03712 | 0.0706 | 0.03178 | 0.01341 |
| | rp | <.0001 | | <.0001 | 0.427 | 0.1306 | 0.4965 | 0.7742 |
| Betel | Pearson's | 0.08635 | 0.27922 | 1 | 0.06318 | 0.02778 | 0.04162 | −0.0314 |
| | rp | 0.0643 | <.0001 | | 0.1761 | 0.5523 | 0.3731 | 0.5017 |
| 19_MMP1 | Pearson's | −0.00535 | 0.03712 | 0.06318 | 1 | 0.20716 | 0.51821 | 0.27268 |
| | rp | 0.9089 | 0.427 | 0.1761 | | <.0001 | <.0001 | <.0001 |
| 1_ANXA2 | Pearson's | 0.08459 | 0.0706 | 0.02778 | 0.20716 | 1 | 0.24789 | 0.30029 |
| | rp | 0.0699 | 0.1306 | 0.5523 | <.0001 | | <.0001 | <.0001 |
| 16_KNG1 | Pearson's | 0.11626 | 0.03178 | 0.04162 | 0.51821 | 0.24789 | 1 | 0.46617 |
| | rp | 0.0126 | 0.4965 | 0.3731 | <.0001 | <.0001 | | <.0001 |
| 13_HSPA5 | Pearson's | 0.13663 | 0.01341 | −0.0314 | 0.27268 | 0.30029 | 0.46617 | 1 |
| | rp | 0.0033 | 0.7742 | 0.5017 | <.0001 | <.0001 | <.0001 | |

1.2 Development of Scoring Scheme

Figure 1B:
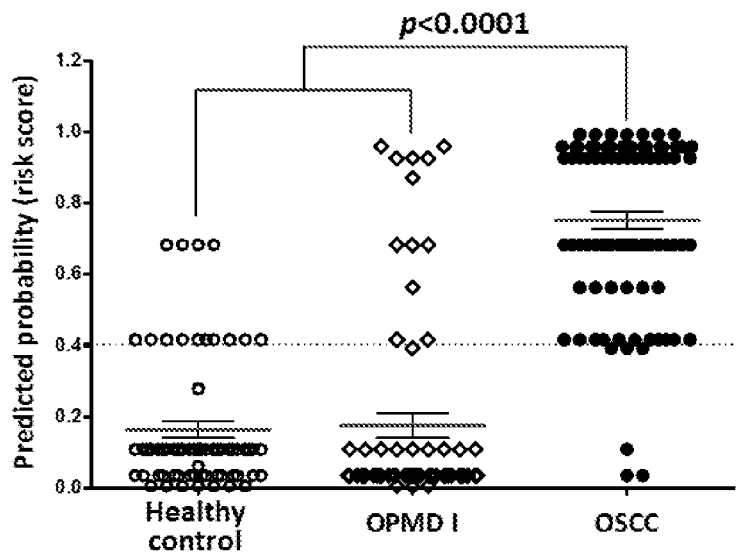
FIG. 1B is a two-dimensional (2-D) dot plot that depicts the risk scores for individual subjects in the healthy control, OPMD I, and OSCC groups, in the training set (n=224).
Figure 1C:
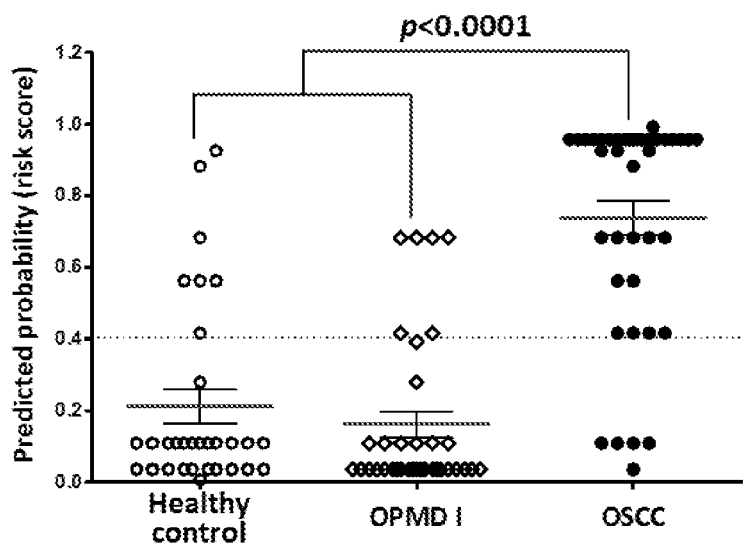
FIG. 1C is a 2-D dot plot that depicts the risk scores for individual subjects in the healthy control, OPMD I, and OSCC groups, in the test set (n=106).
Figure 1D:
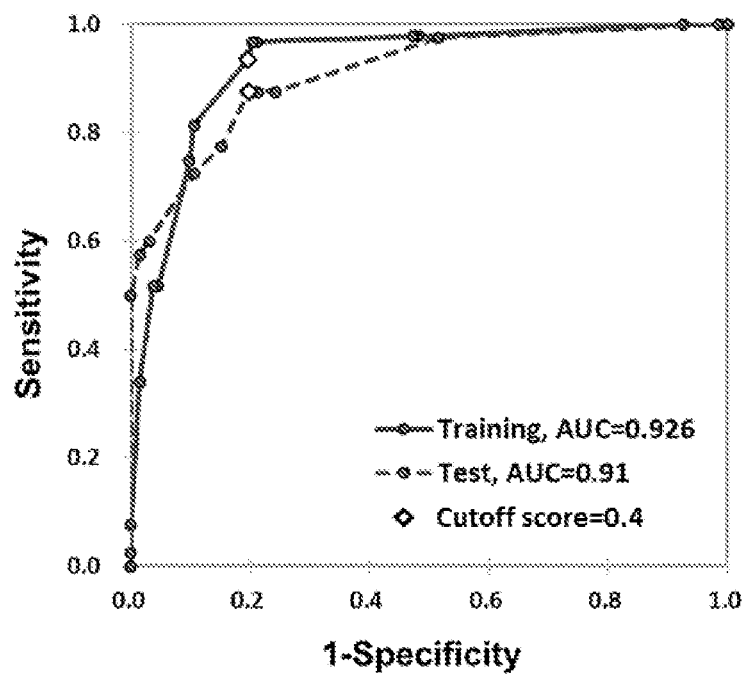
FIG. 1D depicts the area under the curve (AUC), sensitivity, and specificity of both training set and test set.

Next, logistic regression analysis was used to calculate the predictive probability as a risk score, according to the binary results of the four protein markers (i.e., above or below the intrinsic cut-off values). Chi-square tests for the significance of variants in this four-protein panel yielded individual p values of <0.0001, <0.0001, 0.0002, and 0.0007 for MMP1, KNG1, ANXA2, and HSPA5, respectively. The risk score significantly increased from the healthy control (0.16±0.19) and OPMD I (0.18±0.29) groups to the OSCC group (0.75±0.24) in the training set (p<0.0001) (FIG. 1B), and similar results were obtained in the test set (healthy controls, 0.21±0.26; OPMD I, 0.16±0.22; and OSCC, 0.74±0.31; p<0.0001) (FIG. 1C). ROC analysis for non-OSCC vs. OSCC samples indicated that the AUCs for the training and test sets were 0.926 and 0.91, respectively (FIG. 1D). When the cutoff of score was set at 0.4, the four-marker-based scoring scheme gave a high sensitivity (93.4%) and specificity (80.5%) in the training set. For the test set, the sensitivity remained high (87.5%), and the specificity was the same as for the training set (80.5%).

Example 2 Combination of Multiple Markers

After construction of the CART tree (FIG. 1A), the continuous data (numerical variables) of selected markers were dichotomized into binary variables based on their cut-off concentrations at the splitting points. When the observed concentration level was higher than the cut-off value for ANXA2, KNG1 or MMP1, or lower than the cut-off value for HSPA5, positive prediction for OSCC was assigned and given score as 1. In contrast, when the observed concentration level was lower than the cut-off value for ANXA2, KNG1 or MMP1, or higher than the cut-off value for HSPA5, negative prediction for OSCC was assigned and given score as 0. The binary variables generated by CART for the selected markers were included as covariates in a logistic regression to obtain the predicted probability of having OSCC, using the equation:

$$\text{risk score} = \frac{e^{a+b1X1+b2X2+b3X3+b4X4}}{1+e^{a+b1X1+b2X2+b3X3+b4X4}},$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1. And the binary variables generated by CART analysis for these four selected markers were used as covariates and subjected to further logistic regression analysis using the training set samples consisting of non-OSCC (healthy control+OPMD I) and OSCC groups to obtain probability for the prediction of a subject having OSCC. In addition to the four-marker panel, combinations of dual markers from these four markers were also performed (Table 6). Besides, logistic regression analyses using the continuous data (numerical variables) of the four selected markers were also applied to combine these four proteins into four- and two-marker panels (Table 7). The results indicated that each of the four proteins exhibited significant effect (Sig.<0.05) in generating the four-marker panel through ether binary variables or numerical variables. However, the use of HSPA5 to combine ANXA2 or MMP1 as a two-marker panel was not significant in this analysis.

TABLE 6

Generation of marker panels by logistic regression analysis of multiple markers according to their binary variables determined by cut-off concentration.

|  |  | B | S.E. | Wald | df | Sig. | Exp (B) |
| --- | --- | --- | --- | --- | --- | --- | --- |
| 4-marker panel | ANXA2 (>36 ng/ml) | 2.086 | 0.453 | 21.25 | 1 | 4.04E−06 | 8.06 |
|  | HSPA5 (<166.9 ng/ml) | 1.590 | 0.420 | 14.31 | 1 | 1.55E−04 | 4.90 |
|  | KNG1 (>40 ng/ml) | 3.105 | 0.561 | 30.68 | 1 | 3.04E−08 | 22.31 |
|  | MMP1 (>2.772 ng/ml) | 2.619 | 0.364 | 51.79 | 1 | 6.17E−13 | 13.72 |
|  | Constant | −5.016 | 0.659 | 58.00 | 1 | 2.62E−14 | 0.01 |
| 2-marker panel #1 | ANXA2 (>36 ng/ml) | 2.472 | 0.357 | 48.03 | 1 | 4.19E−12 | 11.84 |
|  | HSPA5 (<166.9 ng/ml) | −0.296 | 0.263 | 1.26 | 1 | 2.61E−01 | 0.74 |
|  | Constant | −0.800 | 0.202 | 15.70 | 1 | 7.44E−05 | 0.45 |
| 2-marker panel #2 | ANXA2 (>36 ng/ml) | 2.163 | 0.380 | 32.44 | 1 | 1.23E−08 | 8.70 |
|  | KNG1 (>40 ng/ml) | 2.901 | 0.455 | 40.61 | 1 | 1.86E−10 | 18.19 |
|  | Constant | −3.119 | 0.435 | 51.36 | 1 | 7.68E−13 | 0.04 |
| 2-marker panel #3 | ANXA2 (>36 ng/ml) | 1.940 | 0.412 | 22.19 | 1 | 2.47E−06 | 6.96 |
|  | MMP1 (>2.772 ng/ml) | 2.950 | 0.321 | 84.22 | 1 | 4.42E−20 | 19.11 |
|  | Constant | −1.985 | 0.214 | 86.17 | 1 | 1.65E−20 | 0.14 |
| 2-marker panel #4 | HSPA5 (<166.9 ng/ml) | 0.657 | 0.312 | 4.44 | 1 | 3.50E−02 | 1.93 |
|  | KNG1 (>40 ng/ml) | 3.629 | 0.490 | 54.84 | 1 | 1.31E−13 | 37.66 |
|  | Constant | −3.494 | 0.512 | 46.62 | 1 | 8.63E−12 | 0.03 |
| 2-marker panel #5 | HSPA5 (<166.9 ng/ml) | −0.101 | 0.311 | 0.10 | 1 | 7.47E−01 | 0.90 |
|  | MMP1 (>2.772 ng/ml) | 3.238 | 0.319 | 103.08 | 1 | 3.21E−24 | 25.48 |
|  | Constant | −1.656 | 0.266 | 38.66 | 1 | 5.05E−10 | 0.19 |
| 2-marker panel #6 | KNG1 (>40 ng/ml) | 2.328 | 0.476 | 23.88 | 1 | 1.02E−06 | 10.25 |
|  | MMP1 (>2.772 ng/ml) | 2.698 | 0.325 | 69.10 | 1 | 9.35E−17 | 14.85 |
|  | Constant | −3.293 | 0.451 | 53.27 | 1 | 2.91E−13 | 0.04 |
| 3-marker panel #1 | ANXA2 (>36 ng/ml) | 2.458 | 0.393 | 39.20 | 1 | 3.83E−10 | 11.69 |
|  | HSPA5 (<166.9 ng/ml) | 1.218 | 0.343 | 12.64 | 1 | 3.79E−04 | 3.38 |
|  | KNG1 (>40 ng/ml) | 3.639 | 0.512 | 50.55 | 1 | 1.16E−12 | 38.07 |
|  | Constant | −4.296 | 0.559 | 59.07 | 1 | 1.52E−14 | 0.01 |
| 3-marker panel #2 | ANXA2 (>36 ng/ml) | 2.050 | 0.431 | 22.59 | 1 | 2.01E−06 | 7.77 |
|  | HSPA5 (<166.9 ng/ml) | 0.322 | 0.340 | 0.90 | 1 | 3.43E−01 | 1.38 |
|  | MMP1 (>40 ng/ml) | 3.027 | 0.336 | 81.25 | 1 | 1.99E−19 | 20.64 |
|  | Constant | −2.197 | 0.316 | 48.33 | 1 | 3.60E−12 | 0.11 |

TABLE 6-continued

Generation of marker panels by logistic regression analysis of multiple markers according to their binary variables determined by cut-off concentration.

|  |  | B | S.E. | Wald | df | Sig. | Exp (B) |
|---|---|---|---|---|---|---|---|
| 3-marker panel #3 | ANXA2 (>36 ng/ml) | 1.696 | 0.426 | 15.81 | 1 | 7.00E−05 | 5.45 |
|  | KNG1 (>40 ng/ml) | 2.153 | 0.486 | 19.61 | 1 | 9.48E−06 | 8.61 |
|  | MMP1 (>2.772 ng/ml) | 2.442 | 0.338 | 52.21 | 1 | 5.00E−13 | 11.50 |
|  | Constant | −3.408 | 0.461 | 54.74 | 1 | 1.38E−13 | 0.03 |
| 3-marker panel #4 | HSPA5 (<166.9 ng/ml) | 1.148 | 0.391 | 8.63 | 1 | 3.30E−03 | 3.15 |
|  | KNG1 (>40 ng/ml) | 3.056 | 0.546 | 31.31 | 1 | 2.19E−08 | 21.25 |
|  | MMP1 (>2.772 ng/ml) | 2.859 | 0.342 | 69.82 | 1 | 6.49E−17 | 17.44 |
|  | Constant | −4.428 | 0.615 | 51.90 | 1 | 5.85E−13 | 0.01 |

B: the coefficient for the variables;
S.E.: the standard error around the coefficient;
Wald: Wald chi-square test;
df: the degrees of freedom for the Wald chi-square test;
Sig.: significant p-value; and
Exp (B): the exponentiation of the B coefficient.

TABLE 7

Generation of marker panels by logistic regression analysis of multiple markers according to their numerical variables of concentration.

|  |  | B | S.E. | Wald | df | Sig. | Exp (B) |
|---|---|---|---|---|---|---|---|
| 4-marker panel | ANXA2 | 0.0366 | 0.009 | 15.05 | 1 | 1.05E−04 | 1.04 |
|  | HSPA5 | −0.0016 | 0.001 | 5.48 | 1 | 1.92E−02 | 1.00 |
|  | KNG1 | 0.0012 | 0.001 | 4.01 | 1 | 4.52E−02 | 1.00 |
|  | MMP1 | 0.3357 | 0.065 | 27.02 | 1 | 2.02E−07 | 1.40 |
|  | Constant | −2.2993 | 0.262 | 76.90 | 1 | 1.80E−18 | 0.10 |
| 2-marker panel #1 | ANXA2 | 0.0523 | 0.009 | 34.80 | 1 | 3.65E−09 | 1.05 |
|  | HSPA5 | −0.0003 | 0.000 | 0.53 | 1 | 4.65E−01 | 1.00 |
|  | Constant | −1.5116 | 0.197 | 59.01 | 1 | 1.57E−14 | 0.22 |
| 2-marker panel #2 | ANXA2 | 0.0330 | 0.008 | 18.80 | 1 | 1.45E−05 | 1.03 |
|  | KNG1 | 0.0028 | 0.001 | 17.75 | 1 | 2.52E−05 | 1.00 |
|  | Constant | −1.8642 | 0.210 | 78.83 | 1 | 6.77E−19 | 0.16 |
| 2-marker panel #3 | ANXA2 | 0.0321 | 0.008 | 15.72 | 1 | 7.33E−05 | 1.03 |
|  | MMP1 | 0.3352 | 0.060 | 31.69 | 1 | 1.81E−08 | 1.40 |
|  | Constant | −2.3902 | 0.256 | 86.84 | 1 | 1.17E−20 | 0.09 |
| 2-marker panel #4 | HSPA5 | −0.0006 | 0.000 | 1.88 | 1 | 1.70E−01 | 1.00 |
|  | KNG1 | 0.0049 | 0.001 | 36.89 | 1 | 1.25E−09 | 1.00 |
|  | Constant | −1.3170 | 0.181 | 52.83 | 1 | 3.63E−13 | 0.27 |
| 2-marker panel #5 | HSPA5 | −0.0001 | 0.000 | 0.04 | 1 | 8.51E−01 | 1.00 |
|  | MMP1 | 0.4017 | 0.062 | 41.78 | 1 | 1.02E−10 | 1.49 |
|  | Constant | −1.8367 | 0.221 | 69.29 | 1 | 8.50E−17 | 0.16 |
| 2-marker panel #6 | KNG1 | 0.0014 | 0.001 | 7.18 | 1 | 7.36E−03 | 1.00 |
|  | MMP1 | 0.3649 | 0.062 | 35.00 | 1 | 3.30E−09 | 1.44 |
|  | Constant | −2.0499 | 0.218 | 88.02 | 1 | 6.49E−21 | 0.13 |
| 3-marker panel #1 | ANXA2 | 0.0405 | 0.009 | 21.13 | 1 | 4.30E−06 | 1.04 |
|  | HSPA5 | −0.0014 | 0.001 | 7.22 | 1 | 7.21E−03 | 1.00 |
|  | KNG1 | 0.0036 | 0.001 | 19.25 | 1 | 1.14E−05 | 1.00 |
|  | Constant | −1.7654 | 0.213 | 68.49 | 1 | 1.28E−16 | 0.17 |
| 3-marker panel #2 | ANXA2 | 0.0401 | 0.010 | 17.80 | 1 | 2.46E−05 | 1.04 |
|  | HSPA5 | −0.0013 | 0.001 | 3.82 | 1 | 5.07E−02 | 1.00 |
|  | MMP1 | 0.3534 | 0.062 | 32.18 | 1 | 1.41E−08 | 1.42 |
|  | Constant | −2.2545 | 0.260 | 75.23 | 1 | 4.19E−18 | 0.10 |
| 3-marker panel #3 | ANXA2 | 0.0282 | 0.008 | 11.79 | 1 | 5.94E−04 | 1.03 |
|  | KNG1 | 0.0008 | 0.001 | 2.54 | 1 | 1.11E−01 | 1.00 |
|  | MMP1 | 0.3183 | 0.061 | 27.34 | 1 | 1.71E−07 | 1.37 |
|  | Constant | −2.4437 | 0.261 | 87.72 | 1 | 7.56E−21 | 0.09 |
| 3-marker panel #4 | HSPA5 | −0.0006 | 0.001 | 1.20 | 1 | 2.74E−01 | 1.00 |
|  | KNG1 | 0.0016 | 0.001 | 7.42 | 1 | 6.46E−03 | 1.00 |
|  | MMP1 | 0.3770 | 0.064 | 34.64 | 1 | 3.97E−09 | 1.46 |
|  | Constant | −1.9608 | 0.230 | 72.64 | 1 | 1.55E−17 | 0.14 |

B: the coefficient for the variables;
S.E.: the standard error around the coefficient;
Wald: Wald chi-square test;
df: the degrees of freedom for the Wald chi-square test;
Sig.: significant p-value; and
Exp (B): the exponentiation of the B coefficient.

ROC analyses of different marker panels generated through analysis of binary variables (Tables 8 and 9) or numerical variables (Tables 10 and 11) were obtained for the comparison between non-OSCC (healthy control+OPMD I) and OSCC groups, between OPMD II and OSCC groups, and between non-transformed cases and OSCC-transformed cases in OPMD II patients. Most of the marker panels were found to be useful (AUC 0.65~0.93) for distinguishing OSCC from non-OSCC or OPMD II, and for predicting malignant transformation of OPMD II patients except for the two-marker panel #1, #3, and #5, for which their AUC values were less than 0.6 when used to distinguish non-transformed cases from OSCC-transformed cases in OPMD II patients.

TABLE 8

ROC analyses of different marker panels generated through analysis of binary variables in non-OSCC and OSCC groups.

| | | Non-OSCC (healthy + OPMD I, n = 199) vs. OSCC (n = 131) | | | | |
|---|---|---|---|---|---|---|
| | | Area Under | | | Asymptotic 95% Confidence Interval | |
| | Test Result Variable(s) | the Curve (AUC) | Std. Error[a] | Asymptotic Sig.[b] | Lower Bound | Upper Bound |
| Binary variables | 4-marker panel (ANXA2, HSPA5, KNG1, MMP1) | 0.922 | 0.015 | 1.90E−38 | 0.892 | 0.951 |
| | 2-marker panel #1 (ANXA2, HSPA5) | 0.710 | 0.031 | 1.03E−10 | 0.650 | 0.771 |

TABLE 8-continued

ROC analyses of different marker panels generated through analysis of binary variables in non-OSCC and OSCC groups.

| | | Non-OSCC (healthy + OPMD I, n = 199) vs. OSCC (n = 131) | | | | |
|---|---|---|---|---|---|---|
| | | Area Under | | | Asymptotic 95% Confidence Interval | |
| | Test Result Variable(s) | the Curve (AUC) | Std. Error[a] | Asymptotic Sig.[b] | Lower Bound | Upper Bound |
| | 2-marker panel #2 (ANXA2, KNG1) | 0.836 | 0.022 | 5.49E−25 | 0.793 | 0.879 |
| | 2-marker panel #3 (ANXA2, MMP1) | 0.865 | 0.023 | 3.06E−29 | 0.821 | 0.909 |
| | 2-marker panel #4 (HSPA5, KNG1) | 0.777 | 0.025 | 1.68E−17 | 0.728 | 0.826 |
| | 2-marker panel #5 (HSPA5, MMP1) | 0.828 | 0.025 | 5.87E−24 | 0.779 | 0.878 |
| | 2-marker panel #6 (KNG1, MMP1) | 0.884 | 0.019 | 3.97E−32 | 0.847 | 0.921 |
| | 3-marker panel #1 (ANXA2, HSPA5, KNG1) | 0.863 | 0.020 | 5.45E−29 | 0.824 | 0.903 |
| | 3-marker panel #2 (ANXA2, HSPA5, MMP1) | 0.878 | 0.021 | 3.00E−31 | 0.838 | 0.919 |
| | 3-marker panel #3 (ANXA2, KNG1, MMP1) | 0.907 | 0.017 | 5.57E−36 | 0.875 | 0.940 |
| | 3-marker panel #4 (HSPA5, KNG1, MMP1) | 0.900 | 0.017 | 9.62E−35 | 0.866 | 0.934 |

[a]Under the nonparametric assumption
[b]Null hypothesis: true area = 0.5

TABLE 9

ROC analyses of different marker panels generated through analysis of binary variables in specified groups.

| | | OPMD II (n = 130) vs. OSCC (n = 131) | | | | |
|---|---|---|---|---|---|---|
| | | Area Under | | | Asymptotic 95% Confidence Interval | |
| | Test Result Variable(s) | the Curve (AUC) | Std. Error[a] | Asymptotic Sig.[b] | Lower Bound | Upper Bound |
| Binary variables | 4-marker panel (ANXA2, HSPA5, KNG1, MMP1) | 0.840 | 0.024 | 2.26E−21 | 0.792 | 0.888 |
| | 2-marker panel #1 (ANXA2, HSPA5) | 0.716 | 0.032 | 1.63E−09 | 0.653 | 0.779 |
| | 2-marker panel #2 (ANXA2, KNG1) | 0.765 | 0.029 | 1.29E−13 | 0.708 | 0.822 |
| | 2-marker panel #3 (ANXA2, MMP1) | 0.807 | 0.028 | 1.02E−17 | 0.753 | 0.861 |
| | 2-marker panel #4 (HSPA5, KNG1) | 0.650 | 0.035 | 2.84E−05 | 0.582 | 0.718 |
| | 2-marker panel #5 (HSPA5, MMP1) | 0.733 | 0.032 | 7.05E−11 | 0.670 | 0.797 |
| | 2-marker panel #6 (KNG1, MMP1) | 0.811 | 0.027 | 4.09E−18 | 0.758 | 0.864 |

| | | Non- (n = 70) vs. malignant- (n = 18) transformation | | | | |
|---|---|---|---|---|---|---|
| | | Area Under | | | Asymptotic 95% Confidence Interval | |
| | Test Result Variable(s) | the Curve (AUC) | Std. Error[a] | Asymptotic Sig.[b] | Lower Bound | Upper Bound |
| Binary variables | 4-marker panel (ANXA2, HSPA5, KNG1, MMP1) | 0.716 | 0.057 | 4.82E−03 | 0.605 | 0.828 |
| | 2-marker panel #1 (ANXA2, HSPA5) | 0.571 | 0.077 | 3.52E−01 | 0.421 | 0.722 |
| | 2-marker panel #2 (ANXA2, KNG1) | 0.715 | 0.057 | 5.06E−03 | 0.604 | 0.826 |
| | 2-marker panel #3 (ANXA2, MMP1) | 0.531 | 0.078 | 6.87E−01 | 0.379 | 0.683 |

TABLE 9-continued

ROC analyses of different marker panels generated through analysis of binary variables in specified groups.

| | | | | | |
|---|---|---|---|---|---|
| 2-marker panel #4 (HSPA5, KNG1) | 0.757 | 0.055 | 8.03E−04 | 0.649 | 0.866 |
| 2-marker panel #5 (HSPA5, MMP1) | 0.494 | 0.078 | 9.42E−01 | 0.341 | 0.648 |
| 2-marker panel #6 (KNG1, MMP1) | 0.693 | 0.060 | 1.18E−02 | 0.576 | 0.810 |

[a] Under the nonparametric assumption
[b] Null hypothesis: true area = 0.5

TABLE 10

ROC analyses of different marker panels generated through analysis of numerical variables in Non-OSCC and OSCC groups.

| | | Non-OSCC (healthy + OPMD I, n = 199) vs. OSCC (n = 131) | | | | |
|---|---|---|---|---|---|---|
| | | Area Under | | | Asymptotic 95% Confidence Interval | |
| | Test Result Variable(s) | the Curve (AUC) | Std. Error[a] | Asymptotic Sig.[b] | Lower Bound | Upper Bound |
| Numerical variables | 4-marker panel (ANXA2, HSPA5, KNG1, MMP1) | 0.930 | 0.014 | 6.70E−40 | 0.902 | 0.958 |
| | 2-marker panel #1 (ANXA2, HSPA5) | 0.822 | 0.023 | 4.49E−23 | 0.776 | 0.867 |
| | 2-marker panel #2 (ANXA2, KNG1) | 0.865 | 0.020 | 2.96E−29 | 0.825 | 0.905 |
| | 2-marker panel #3 (ANXA2, MMP1) | 0.917 | 0.016 | 1.10E−37 | 0.886 | 0.949 |
| | 2-marker panel #4 (HSPA5, KNG1) | 0.891 | 0.018 | 3.18E−33 | 0.855 | 0.927 |
| | 2-marker panel #5 (HSPA5, MMP1) | 0.857 | 0.025 | 5.67E−28 | 0.807 | 0.906 |
| | 2-marker panel #6 (KNG1, MMP1) | 0.917 | 0.015 | 1.13E−37 | 0.887 | 0.948 |
| | 3-marker panel #1 (ANXA2, HSPA5, KNG1) | 0.892 | 0.018 | 2.23E−33 | 0.856 | 0.928 |
| | 3-marker panel #2 (ANXA2, HSPA5, MMP1) | 0.923 | 0.015 | 1.41E−38 | 0.892 | 0.953 |
| | 3-marker panel #3 (ANXA2, KNG1, MMP1) | 0.922 | 0.015 | 2.01E−38 | 0.891 | 0.952 |
| | 3-marker panel #4 (HSPA5, KNG1, MMP1) | 0.913 | 0.017 | 6.86E−37 | 0.879 | 0.946 |

[a] Under the nonparametric assumption
[b] Null hypothesis: true area = 0.5

TABLE 11

ROC analyses of different marker panels generated through analysis of numerical variables in specified groups.

| | | OPMD II (n = 130) vs. OSCC (n = 131) | | | | |
|---|---|---|---|---|---|---|
| | | Area Under | | | Asymptotic 95% Confidence Interval | |
| | Test Result Variable(s) | the Curve (AUC) | Std. Error[a] | Asymptotic Sig.[b] | Lower Bound | Upper Bound |
| Numerical variables | 4-marker panel (ANXA2, HSPA5, KNG1, MMP1) | 0.870 | 0.022 | 5.02E−25 | 0.827 | 0.913 |
| | 2-marker panel #1 (ANXA2, HSPA5) | 0.780 | 0.028 | 4.98E−15 | 0.725 | 0.835 |
| | 2-marker panel #2 (ANXA2, KNG1) | 0.819 | 0.026 | 4.92E−19 | 0.769 | 0.869 |
| | 2-marker panel #3 (ANXA2, MMP1) | 0.855 | 0.023 | 3.14E−23 | 0.810 | 0.901 |

TABLE 11-continued

ROC analyses of different marker panels generated through analysis of numerical variables in specified groups.

| | | | | | |
|---|---|---|---|---|---|
| 2-marker panel #4 (HSPA5, KNG1) | 0.822 | 0.026 | 2.64E−19 | 0.771 | 0.872 |
| 2-marker panel #5 (HSPA5, MMP1) | 0.802 | 0.029 | 3.19E−17 | 0.745 | 0.859 |
| 2-marker panel #6 (KNG1, MMP1) | 0.862 | 0.023 | 4.65E−24 | 0.817 | 0.907 |

| | | Non- (n = 70) vs. malignant- (n = 18) transformation | | | |
|---|---|---|---|---|---|
| | | Area Under the Curve (AUC) | Std. Error[a] | Asymptotic Sig.[b] | Asymptotic 95% Confidence Interval |
| | | | | | Lower Bound / Upper Bound |
| Numerical variables | 4-marker panel (ANXA2, HSPA5, KNG1, MMP1) | 0.671 | 0.067 | 2.61E−02 | 0.539 / 0.802 |
| | 2-marker panel #1 (ANXA2, HSPA5) | 0.555 | 0.080 | 4.75E−01 | 0.398 / 0.711 |
| | 2-marker panel #2 (ANXA2, KNG1) | 0.734 | 0.055 | 2.28E−03 | 0.626 / 0.842 |
| | 2-marker panel #3 (ANXA2, MMP1) | 0.525 | 0.084 | 7.48E−01 | 0.361 / 0.688 |
| | 2-marker panel #4 (HSPA5, KNG1) | 0.810 | 0.048 | 5.48E−05 | 0.716 / 0.903 |
| | 2-marker panel #5 (HSPA5, MMP1) | 0.487 | 0.084 | 8.60E−01 | 0.321 / 0.652 |
| | 2-marker panel #6 (KNG1, MMP1) | 0.658 | 0.070 | 3.95E−02 | 0.521 / 0.795 |

[a] Under the nonparametric assumption
[b] Null hypothesis: true area = 0.5

The risk score of various markers' panels generated through analysis of binary variables (Table 12) or numerical variables (Table 13) were obtained for the comparison between non-OSCC (healthy control+OPMD I) and OSCC groups. When the cut-off values of score at 0.4 exhibited high negative predictive value (81.9%-93.6%, except for except for 2-marker panel #1, #2 and #4); at 0.6 exhibited high positive predictive value (81.4%-93.4%, except for except for 3-marker panel #1 and 2-marker panel #4). The data indicated that the cut-off values of score at 0.4 or 0.6 exhibited high accuracy (78.8%-86.7%, except for 2-marker panel #1, #2 and #4) for distinguishing non-OSCC (healthy control+OPMD I) subjects and OSCC patients.

TABLE 12

Efficacy of marker panels for discriminating OSCC from healthy control + OPMI group according to binary result of markers determined by cut-off concentration

| panel | Markers in panel equation of risk score (RS = e^f(x)/(1 + e^f(x))) | Cut-off value of RS | Sensitivity | Specificity | Accuracy | Positive predictive value | Negative predictive value |
|---|---|---|---|---|---|---|---|
| 4-marker panel | ANXA2 (A), HSPA5 (H), KNG1 (K), MMP1 (M) | 0.4 | 91.6% | 80.4% | 84.8% | 75.5% | 93.6% |
| | $f(x) = 2.086 * X_A + 1.590 * X_H + 3.105 * X_K + 2.619 * X_M − 5.016$ | 0.6 | 74.0% | 89.9% | 83.6% | 82.9% | 84.0% |
| 3-marker panel #1 | ANXA2 (A), HSPA5 (H), KNG1 (K) | 0.4 | 71.8% | 86.9% | 80.9% | 78.3% | 82.4% |
| | $f(x) = 2.458 * X_A + 1.218 * X_H + 3.639 * X_K − 4.296$ | 0.6 | 71.8% | 86.9% | 80.9% | 78.3% | 82.4% |
| 3-marker panel #2 | ANXA2 (A), HSPA5 (H), MMP1 (M) | 0.4 | 82.4% | 84.9% | 83.9% | 78.3% | 88.0% |
| | $f(x) = 2.050 * X_A + 0.322 * X_H + 3.027 * X_M − 2.197$ | 0.6 | 75.6% | 89.4% | 83.9% | 82.5% | 84.8% |
| 3-marker panel #3 | ANXA2 (A), KNG1 (K), MMP1 (M) | 0.4 | 80.2% | 87.9% | 84.8% | 81.4% | 87.1% |
| | $f(x) = 1.696 * X_A + 2.153 * X_K + 2.442 * X_M − 3.408$ | 0.6 | 80.2% | 87.9% | 84.8% | 81.4% | 87.1% |
| 3-marker panel #4 | HSPA5 (H), KNG1 (K), MMP1 (M) | 0.4 | 85.5% | 82.9% | 83.9% | 76.7% | 89.7% |
| | $f(x) = 1.1481 * X_H + 3.056 * X_K + 2.859 * X_M − 4.428$ | 0.6 | 73.3% | 91.0% | 83.9% | 84.2% | 83.8% |
| 2-marker panel #1 | ANXA2 (A), HSPA5 (H) | 0.4 | 45.8% | 94.0% | 74.8% | 83.3% | 72.5% |
| | $f(x) = 2.472 * X_A − 0.296 * X_H − 0.800$ | 0.6 | 45.8% | 94.0% | 74.8% | 83.3% | 72.5% |
| 2-marker panel #2 | ANXA2 (A), KNG1 (K) | 0.4 | 95.4% | 54.3% | 70.6% | 57.9% | 94.7% |
| | $f(x) = 2.163 * X_A + 2.901 * X_K − 3.119$ | 0.6 | 45.8% | 96.5% | 76.4% | 89.6% | 73.0% |
| 2-marker panel #3 | ANXA2 (A), MMP1 (M) | 0.4 | 82.4% | 84.9% | 83.9% | 78.3% | 88.0% |
| | $f(x) = 1.940 * X_A + 2.950 * X_M − 1.985$ | 0.6 | 75.6% | 89.4% | 83.9% | 82.5% | 84.8% |
| 2-marker panel #4 | HSPA5 (H), KNG1 (K) | 0.4 | 95.4% | 54.3% | 70.6% | 57.9% | 94.7% |
| | $f(x) = −0.657 * X_H + 3.629 * X_K − 3.494$ | 0.6 | 32.8% | 89.9% | 67.3% | 68.3% | 67.0% |
| 2-marker panel #5 | HSPA5 (H), MMP1 (M) | 0.4 | 75.6% | 89.4% | 83.9% | 82.5% | 84.8% |
| | $f(x) = −0.101 * X_H + 3.238 * X_M − 1.656$ | 0.6 | 75.6% | 89.4% | 83.9% | 82.5% | 84.8% |

TABLE 12-continued

Efficacy of marker panels for discriminating OSCC from healthy control + OPMI group according to binary result of markers determined by cut-off concentration

| panel | Markers in panel equation of risk score (RS = e^f(x)/(1 + e^f(x))) | Cut-off value of RS | Sensitivity | Specificity | Accuracy | Positive predictive value | Negative predictive value |
|---|---|---|---|---|---|---|---|
| 2-marker panel #6 | KNG1 (K), MMP1 (M) | 0.4 | 73.3% | 91.0% | 83.9% | 84.2% | 83.8% |
| | f(x) = 2.328 * $X_K$ + 2.698 * $X_M$ − 3.293 | 0.6 | 73.3% | 91.0% | 83.9% | 84.2% | 83.8% |

$X_A$ is the binary result of ANXA2 determined by cut-off concentration (>36 ng/mL as positive)
$X_H$ is the binary result of HSPA5 determined by cut-off concentration (<166.9 ng/mL as positive)
$X_K$ is the binary result of KNG1 determined by cut-off concentration (>40 ng/mL as positive)
$X_M$ is the binary result of MMP1 determined by cut-off concentration (>2.772 ng/mL as positive)

TABLE 13

Efficacy of marker panels for discriminating OSCC from healthy control + OPMI group according to numerical concentration of markers

| panel | Markers in panel equation of risk score (RS = e^f(x)/(1 + e^f(x))) | Cut-off value of RS | Sensitivity | Specificity | Accuracy | Positive predictive value | Negative predictive value |
|---|---|---|---|---|---|---|---|
| 4-marker panel | ANXA2 (A), HSPA5 (H), KNG1 (K), MMP1 (M) | 0.4 | 77.1% | 93.0% | 86.7% | 87.8% | 86.0% |
| | f(x) = 0.0366 * $X_A$ − 0.0016 * $X_H$ + 0.0012 * $X_K$ + 0.3357 * $X_M$ − 2.2993 | 0.6 | 67.9% | 96.0% | 84.8% | 91.8% | 82.0% |
| 3-marker panel #1 | ANXA2 (A), HSPA5 (H), KNG1 (K) | 0.4 | 70.2% | 88.9% | 81.5% | 80.7% | 81.9% |
| | f(x) = 0.0405 * $X_A$ − 0.0014 * $X_H$ + 0.0036 * $X_K$ − 1.7654 | 0.6 | 52.7% | 96.0% | 78.8% | 89.6% | 75.5% |
| 3-marker panel #2 | ANXA2 (A), HSPA5 (H), MMP1 (M) | 0.4 | 75.6% | 92.5% | 85.8% | 86.8% | 85.2% |
| | f(x) = 0.0401 * $X_A$ − 0.0013 * $X_H$ + 0.3534 * $X_M$ − 2.2545 | 0.6 | 67.2% | 96.5% | 84.8% | 92.6% | 81.7% |
| 3-marker panel #3 | ANXA2 (A), KNG1 (K), MMP1 (M) | 0.4 | 74.0% | 93.5% | 85.8% | 88.2% | 84.5% |
| | f(x) = 0.0282 * $X_A$ + 0.0008 * $X_K$ + 0.3183 * $X_M$ − 2.4437 | 0.6 | 67.9% | 96.5% | 85.2% | 92.7% | 82.1% |
| 3-marker panel #4 | HSPA5 (H), KNG1 (K), MMP1 (M) | 0.4 | 74.0% | 93.0% | 85.5% | 87.4% | 84.5% |
| | f(x) = −0.0006 * $X_H$ + 0.0016 * $X_K$ + 0.3770 * $X_M$ − 1.9608 | 0.6 | 66.4% | 96.0% | 84.2% | 91.6% | 81.3% |
| 2-marker panel #1 | ANXA2 (A), HSPA5 (H) | 0.4 | 59.5% | 86.9% | 76.1% | 75.0% | 76.5% |
| | f(x) = 0.0523 * $X_A$ − 0.0003 * $X_H$ − 1.5116 | 0.6 | 41.2% | 94.5% | 73.3% | 83.1% | 70.9% |
| 2-marker panel #2 | ANXA2 (A), KNG1 (K) | 0.4 | 67.2% | 88.9% | 80.3% | 80.0% | 80.5% |
| | f(x) = 0.0330 * $X_A$ + 0.0028 * $X_K$ − 1.8642 | 0.6 | 51.1% | 95.0% | 77.6% | 87.0% | 74.7% |
| 2-marker panel #3 | ANXA2 (A), MMP1 (M) | 0.4 | 74.8% | 94.0% | 86.4% | 89.1% | 85.0% |
| | f(x) = 0.0321 * $X_A$ + 0.3352 * $X_M$ − 2.3902 | 0.6 | 67.2% | 96.5% | 84.8% | 92.6% | 81.7% |
| 2-marker panel #4 | HSPA5 (H), KNG1 (K) | 0.4 | 61.8% | 91.5% | 79.7% | 82.7% | 78.4% |
| | f(x) = −0.0006 * $X_H$ + 0.0049 * $X_K$ − 1.3170 | 0.6 | 44.3% | 97.0% | 76.1% | 90.6% | 72.6% |
| 2-marker panel #5 | HSPA5 (H), MMP1 (M) | 0.4 | 71.0% | 92.5% | 83.9% | 86.1% | 82.9% |
| | f(x) = −0.0001 * $X_H$ + 0.4017 * $X_M$ − 1.8367 | 0.6 | 64.9% | 97.0% | 84.2% | 93.4% | 80.8% |
| 2-marker panel #6 | KNG1 (K), MMP1 (M) | 0.4 | 74.0% | 93.0% | 85.5% | 87.4% | 84.5% |
| | f(x) = 0.0014 * $X_K$ + 0.3649 * $X_M$ − 2.0499 | 0.6 | 65.6% | 96.0% | 83.9% | 91.5% | 80.9% |

$X_A$ is the numerical concentration of ANXA2 (ng/mL)
$X_H$ is the numerical concentration of HSPA5 (ng/mL)
$X_K$ is the numerical concentration of KNG1 (ng/mL)
$X_M$ is the numerical concentration of MMP1 (ng/mL)

Example 3 Risk Scores in Stage I-IV OSCC Patients

Figure 2:
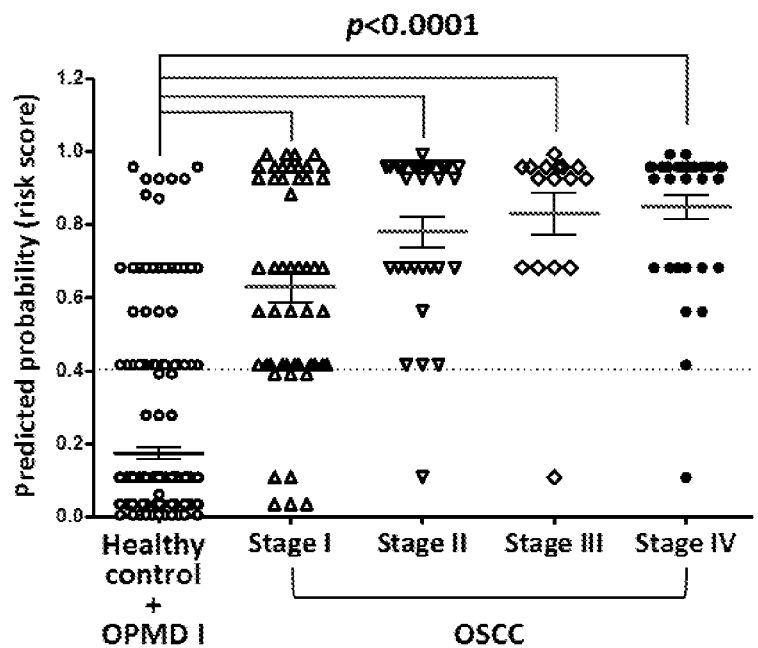
FIG. 2 is a 2-D dot plot analysis of the four-protein-panel-based risk scores of OSCC patients in stages I to IV (n=50, 29, 16, and 36, respectively) compared with the non-OSCC group (healthy control+OPMD I; n=199).

The present invention included 50 stage I, 29 stage II, 16 stage III, and 36 stage IV OSCC patients. The four-marker-based scoring scheme was used to calculate the risk scores for these patients. As shown in FIG. 2, the risk scores increased gradually from the early to advanced stages (stage I, 0.63±0.29; stage II, 0.78±0.23; stage III, 0.83±0.23; and stage IV, 0.85±0.20). More importantly, there was a significantly higher risk score in stage I OSCC compared to the non-OSCC group (healthy controls+OPMD I; average score, 0.17±0.24; p<0.0001). Moreover, 84% (42/50), 97% (28/29), 94% (15/16) and 97% (35/36) of the stage I, II, III, and IV OSCC patients, respectively, had risk scores>0.4 (Table 14), indicating that the four-protein-panel-based scoring system has a good potential to detect a significant portion (>80%) of stage I OSCC patients.

TABLE 14

The percentage of subjects with risk scores >0.4 in OSCC patients of stages I to IV

| | | Risk score >0.4 | |
|---|---|---|---|
| OSCC stage | Case No. | Negative case No. (%) | Positive case No. (%) |
| I | 50 | 8 (16%) | 42 (84%) |
| II | 29 | 1 (3%) | 28 (97%) |
| III | 16 | 1 (6%) | 15 (94%) |
| IV | 36 | 1 (3%) | 35 (97%) |
| Total | 131 | 11 (8.4%) | 120 (91.6%) |

Example 4 Risk Scores in OPMD II Patients and their Follow-Up Results

Figure 3:
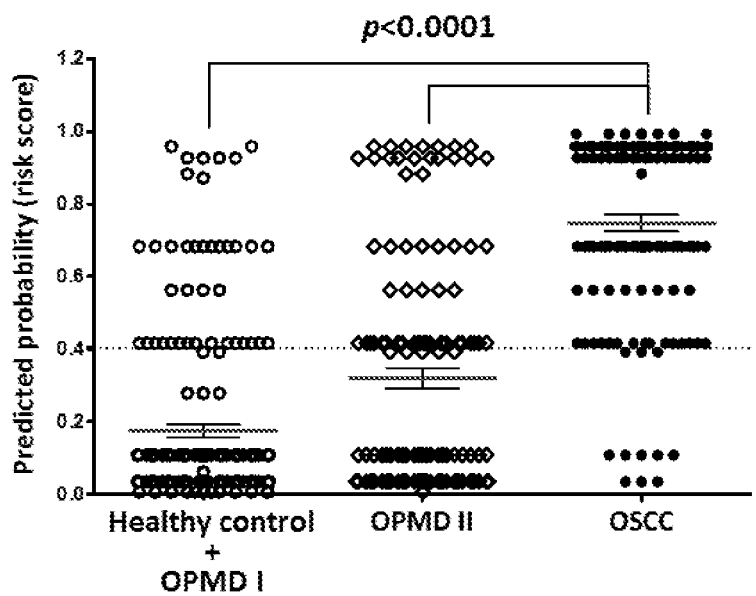
FIG. 3 is a 2-D dot plot analysis of the four-protein-panel-based risk scores of the OPMD II group (n=130) compared with those of the non-OSCC group (healthy controls+OPMD I; n=199) and the OSCC group (n=131).

Since the OPMD II lesions may comprise a mixture of potentially malignant cells, malignant cells, and normal cells, it is difficult to distinguish OSCC from OPMD II. However, the average risk score of the OPMD II group (0.32±0.33) was higher than that of the non-OSCC group (healthy controls+OPMD I; 0.17±0.24), but significantly lower than that of OSCC group (0.75±0.26) (FIG. 3). Notably, 42% (55/130) of the OPMD II cases had risk scores>0.4 (Table 15). This observation is consistent with the argument that OPMD II lesions may harbor malignant cells.

TABLE 15

The percentage of subjects with risk scores >0.4 in the non-OSCC (healthy controls + OPMD I) and OPMD II groups.

| | | Risk score >0.4 | |
|---|---|---|---|
| Group | Case No. | Negative case No. (%) | Positive case No. (%) |
| Healthy control + OPMD I | 199 | 160 (80%) | 39 (20%) |
| OPMD II | 130 | 75 (58%) | 55 (42%) |

In addition to the need to detect OSCC, another important open issue is our lack of ability to predict or monitor malignant transformation in a large population of OPMDs, especially the high-risk OPMD II group. Among the 233 OPMD patients enrolled in the present invention, the malignant statuses of 153 cases (65 OPMD I and 88 OPMD II) were retrospectively retrieved from follow-up periods ranging from 13.5 to 76.6 months. Eighteen cases in the OPMD II group showed malignant transformation to OSCC within 1.2 to 65.5 months; these cases included one each of erythroleukoplakia, erythroplakia plus submucous fibrosis, submucous fibrosis, and speckle leukoplakia, four of verrucous hyperplasia, and 10 of verrucous hyperplasia plus submucous fibrosis. In contrast, no malignant transformation was observed during follow-up in the OPMD I group. The malignant transformation rate among the OPMD patients was 11.8% (18/153), which falls within the previously reported range. The risk score of various markers' panels generated through analysis of binary variables (Table 16) or numerical variables (Table 17) were obtained in the OPMD II groups. In patients harboring risk scores≥0.4 showed higher OSCC transforming rate than which <0.4 in most marker panels except in two-marker panel #1. According to 4-marker panel in Table 16, for example, there were 37 cases showed risk scores≥0.4, and of these cases, 37.8% (14 out of 37) transformed to OSCC during follow-up. This transformation rate was much higher than that of the 51 OPMD II cases harboring risk scores<0.4 (7.8%; 4/51) (Table 16). Of the 18 OSCC-transformed cases, 77.8% (14/18) had risk scores>0.4.

TABLE 16

The OSCC transformation rate during 88 follow-up in OPMD II subjects with binary-marker panel-based risk scores

| panel | Markers in panel equation of risk score (RS) (RS = e^f(x)/(1 + e^f(x))) | % of patients transform to OSCC | |
|---|---|---|---|
| | | RS < 0.4 | RS ≥ 0.4 |
| 4-marker panel | ANXA2 (A), HSPA5 (H), KNG1 (K), MMP1 (M) $f(x) = 2.086*X_A + 1.590*X_H + 3.105*X_K + 2.619*X_M - 5.016$ | 7.8% (4/51) | 37.8% (14/37) |
| 3-marker panel #1 | ANXA2 (A), HSPA5 (H), KNG1 (K) $f(x) = 2.458*X_A + 1.218*X_H + 3.639*X_K - 4.296$ | 12.5% (7/56) | 34.4% (11/32) |
| 3-marker panel #2 | ANXA2 (A), HSPA5 (H), MMP1 (M) $f(x) = 2.050*X_A + 0.322*X_H + 3.027*X_M - 2.197$ | 19.0% (12/63) | 24.0% (6/25) |
| 3-marker panel #3 | ANXA2 (A), KNG1 (K), MMP1 (M) $f(x) = 1.696*X_A + 2.153*X_K + 2.442*X_M - 3.408$ | 17.9% (12/67) | 28.6% (6/21) |
| 3-marker panel #4 | HSPA5 (H), KNG1 (K), MMP1 (M) $f(x) = 1.1481*X_H + 3.056*X_K + 2.859*X_M - 4.428$ | 9.3% (5/54) | 38.2% (13/34) |
| 2-marker panel #1 | ANXA2 (A), HSPA5 (H) $f(x) = 2.472*X_A - 0.296*X_H - 0.800$ | 20.5% (16/78) | 20.0% (2/10) |
| 2-marker panel #2 | ANXA2 (A), KNG1 (K) $f(x) = 2.163*X_A + 2.901*X_K - 3.119$ | 2.6% (1/39) | 34.7% (17/49) |
| 2-marker panel #3 | ANXA2 (A), MMP1 (M) $f(x) = 1.940*X_A + 2.950*X_M - 1.985$ | 19.0% (12/63) | 24.0% (6/25) |
| 2-marker panel #4 | HSPA5 (H), KNG1 (K) $f(x) = -0.657*X_H + 3.629*X_K - 3.494$ | 15.9% (10/63) | 32.0% (8/25) |
| 2-marker panel #5 | HSPA5 (H), MMP1 (M) $f(x) = -0.101*X_H + 3.238*X_M - 1.656$ | 19.1% (13/68) | 25.0% (5/20) |

TABLE 16-continued

The OSCC transformation rate during 88 follow-up in OPMD
II subjects with binary-marker panel-based risk scores

| panel | Markers in panel equation of risk score (RS) (RS = e^f(x)/(1 + e^f(x))) | % of patients transform to OSCC | |
|---|---|---|---|
| | | RS < 0.4 | RS ≥ 0.4 |
| 2-marker panel #6 KNG1 (K), MMP1 (M) f(x) = 2.328*$X_K$ + 2.698*$X_M$ − 3.293 | | 18.1% (13/72) | 31.3% (5/16) |

$X_A$ is the binary result of ANXA2 determined by cut-off concentration (>36 ng/mL as positive)
$X_H$ is the binary result of HSPA5 determined by cut-off concentration (<166.9 ng/mL as positive)
$X_K$ is the binary result of KNG1 determined by cut-off concentration (>40 ng/mL as positive)
$X_M$ is the binary result of MMP1 determined by cut-off concentration (>2.772 ng/mL as positive)

TABLE 17

The OSCC transformation rate during 88 follow-up in OPMD
II subjects with numerical-marker panel-based risk scores

| panel | Markers in panel equation of risk score (RS) (RS = e^f(x)/(1 + e^f(x))) | % of patients transform to OSCC | |
|---|---|---|---|
| | | RS < 0.4 | RS > 0.4 |
| 4-marker panel ANXA2 (A), HSPA5 (H), KNG1 (K), MMP1 (M) f(x) = 0.0366*$X_A$ − 0.0016*$X_H$ + 0.0012*$X_K$ + 0.3357*$X_M$ − 2.2993 | | 19.5% (15/77) | 27.3% (3/11) |
| 3-marker panel #1 ANXA2 (A), HSPA5 (H), KNG1 (K) f(x) = 0.0405*$X_A$ − 0.0014*$X_H$ + 0.0036*$X_K$ − 1.7654 | | 19.1% (13/68) | 25.0% (5/20) |
| 3-marker panel #2 ANXA2 (A), HSPA5 (H), MMP1 (M) f(x) = 0.0401*$X_A$ − 0.0013*$X_H$ + 0.3534*$X_M$ − 2.2545 | | 20.0% (15/75) | 23.1% (3/13) |
| 3-marker panel #3 ANXA2 (A), KNG1 (K), MMP1 (M) f(x) = 0.0282*$X_A$ + 0.0008*$X_K$ + 0.3183*$X_M$ − 2.4437 | | 19.5% (15/77) | 27.3% (3/11) |
| 3-marker panel #4 HSPA5 (H), KNG1 (K), MMP1 (M) f(x) = −0.0006*$X_H$ + 0.0016*$X_K$ + 0.3770*$X_M$ − 1.9608 | | 17.6% (13/74) | 35.7% (5/14) |
| 2-marker panel #1 ANXA2 (A), HSPA5 (H) f(x) = 0.0523*$X_A$ − 0.0003*$X_H$ − 1.5116 | | 18.3% (13/71) | 29.4% (5/17) |
| 2-marker panel #2 ANXA2 (A), KNG1 (K) f(x) = 0.0330*$X_A$ + 0.0028*$X_K$ − 1.8642 | | 19.4% (14/72) | 25.0% (4/16) |
| 2-marker panel #3 ANXA2 (A), MMP1 (M) f(x) = 0.0321*$X_A$ + 0.3352*$X_M$ − 2.3902 | | 19.5% (15/77) | 27.3% (3/11) |
| 2-marker panel #4 HSPA5 (H), KNG1 (K) f(x) = −0.0006*$X_H$ + 0.0049*$X_K$ − 1.3170 | | 16.4% (12/73) | 40.0% (6/15) |
| 2-marker panel #5 HSPA5 (H), MMP1 (M) f(x) = −0.0001*$X_H$ + 0.4017*$X_M$ − 1.8367 | | 17.6% (13/74) | 35.7% (5/14) |
| 2-marker panel #6 KNG1 (K), MMP1 (M) f(x) = 0.0014*$X_K$ + 0.3649*$X_M$ − 2.0499 | | 18.4% (14/76) | 33.3% (4/12) |

$X_A$ is the numerical concentration of ANXA2 (ng/mL)
$X_H$ is the numerical concentration of HSPA5 (ng/mL)
$X_K$ is the numerical concentration of KNG1 (ng/mL)
$X_M$ is the numerical concentration of MMP1 (ng/mL)

The early detection of OSCC is complicated by the pathological complexity seen in the various types of OPMD lesions. About 1400 papers have investigated candidate proteins that are differentially elevated in body fluids or tissues of OSCC patients versus those of healthy control individuals. However, no molecular marker has yet proven clinically useful for detecting early-stage disease and/or providing an early warning for the transformation of high-risk lesions (i.e., among cases of OPMD II). In the present invention, a panel of four proteins was developed that are readily detected in saliva and together could effectively distinguish OSCC patients (including stage I disease) from non-OSCC subjects recruited through the Taiwan's Oral Cancer Screening Program. This four-protein panel can be used to evaluate the risk of malignant progression from clinically suspicious or high-risk OPMD II lesions, and thus prevent diagnostic delay. In the 88 OPMD II subjects with follow-up data, 18 developed cancer within 5 years; of them, 14 had high-risk scores (>0.4) measured in saliva samples taken upon the first diagnosis of OPMD II.

The present invention offers a practical foundation for clinical trials examining the ability of this four-marker panel to: (i) detect OSCC in high-risk populations, such as those enrolled in the Taiwan's Oral Cancer Screening Program; (ii) assess the risk for the presence of malignant cells in clinically suspicious lesions; (iii) select OPMD II patients for close follow-up; and (iv) monitor treatment response or recurrence. The four-protein panel could be used as a diagnostic adjunct to eliminate diagnosis delay due to patient delay by patients themselves or professional delay of diagnosis by the primary physician. The cutoff values of scores at 0.4 and 0.6, which showed high sensitivity (91.6%) and high specificity (90%), respectively, to discriminate OSCC from non-OSCC (Table 18), might be used for OSCC detection in high-risk population. Based on the result, (i) subjects with high-risk score (≥0.6) will need to undergo re-biopsy or to comprehensively detect occult tumor; (ii) subjects with medium risk score (≥0.4 and <0.6) will be followed up twice per year; (iii) subjects with low risk score (<0.4) can be managed following the current follow-up protocol (once per 2 years); (iv) subjects with low risk score (<0.4) and also with normal mucosa might be a meaningful indicator for more regressive management, such as extending the interval of follow-up check.

TABLE 18

The performance (sensitivity and specificity) of using cutoff values of scores at 0.4 and 0.6 to discriminate Non-OSCC (Healthy control + OPMD I) from OSCC group

| | Healthy control + OPMD I vs. OSCC | |
|---|---|---|
| AUC | 0.922 | |
| Cutoff of score | ≥0.4 | ≥0.6 |
| Sensitivity | 91.60% | 74.05% |
| Specificity | 80.40% | 89.95% |

Several findings in the present invention are worth noting. Over the past two decades, more than one thousands of published studies have investigated biomarkers for head and neck cancers, including OSCC. However, few of the reported biomarkers have moved into clinical practice. We believe that this reflects an insufficient effort to compare candidate biomarkers against one another in adequate case and control samples, in efforts to identify groups of biomarkers that provide enough predictive value to properly guide medical care. Here, we present a solution that overcomes this major barrier by: (i) using intensive literature reviews to select candidate proteins that have been tested in multiple types of clinical samples by our group and others; and (ii) comparing case (OSCC) and control (healthy control and OPMD I) samples from a high-risk population that shares similar risk factors (smoking and betel nut chewing). The detection sensitivity for the four selected proteins in saliva (which is site-specific for oral cavity cancers) was 87.5-93.4%. Moreover, the marker panel successfully detected 88% (70 out of 79) of patients with early-stage OSCC (stage I or II), and 92% (120 out of 131) of all OSCC patients. This indicates the possibility of examining protein biomarkers in saliva non-invasively collected from the disease site for early OSCC detection.

Several interacting factors can delay the diagnosis of OSCC, affecting the prognosis and survival of these patients. For example, OSCC can arise from all tissues within the oral cavity, and diagnosis is often complicated by the presence of various types of OPMDs. Visual screening of lesions is currently accepted as the first-line method of diagnosis, but the success of this strategy more or less depends on personal experience. In some cases, such as severe submucous fibrosis, patients are unable to fully open their mouths to enable extensive investigation or biopsy. In addition, some individuals may present with multiple types of lesions. Moreover, the pathological testing performed in clinical practice is usually limited to a single sampling (biopsy), which could miss the presence of cancer cells in a lesion with mixed OPMD types. The analysis of the four-protein panel in saliva samples, which comprise a mixture collected from the entire mouth, may overcome these problems.

The specificity of the four-protein panel is about 80%. In the future, this could likely be improved by combining it with other types of salivary cancer-cell markers, such as tumor-specific microRNAs or DNA mutations. In terms of limitations, the present invention includes a somewhat small number of subjects in each of the four groups, and all subjects were collected from two clinical sites within a single hospital. Future clinical trials with larger numbers of samples collected from multiple hospitals will be needed to evaluate the performance of the four-protein panel for the early detection of OSCC. In addition, the present work was conducted using retrospective samples. A prospective study with intended-use samples is needed to further validate the clinical utility of the new biomarker panel.

For a successful biomarker verification study, the following criteria such as multiplexed assay, high sensitivity and specificity, and broad dynamic range for detection are required. In the present invention, the protein (peptide) levels in saliva were analyzed by LC-MRM-MS, which is an established technology for performing both qualitative and quantitative measurements. We were able to detect the 28 candidate protein markers at concentrations ranging from 1 ng/ml to 2000 ng/ml. This detection limit is as good as the specificity of an antibody (such as that used in ELISA), but LC-MRM-MS can avoid the bias that could be introduced by off-target antibody effects.

In summary, early detection of OSCC is critical for successful and cost-effective disease control and patient management. We do not currently have any molecular marker available for the clinical diagnosis or monitoring of OSCC. However, we herein describe the development and validation of a clinically applicable salivary protein biomarker panel for the early detection of OSCC and the monitoring of patients with high risk OPMDs. With the support of the Ministry of Health and Welfare in Taiwan, we are currently planning a clinical trial in which larger numbers of OSCC and OPMD II patients will be collected from the high-risk populations of two additional hospitals.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of determining whether a subject has or is at risk of developing oral squamous cell carcinoma (OSCC), comprising,
   (a) obtaining a biological sample from the subject;
   (b) determining the concentration of at least two target polypeptides in the biological sample by the steps of:
      (b-1) selecting at least two surrogate peptides corresponding to the at least two target polypeptides, wherein each of the at least two surrogate peptides is selected from the group consisting of ANXA2 surrogate peptide, HSPA5 surrogate peptide, KNG1 surrogate peptide, and MMP1 surrogate peptide, wherein the ANXA2 surrogate peptide comprises the amino acid sequence of SEQ ID NO: 5; the HSPA5 surrogate peptide comprises the amino acid sequence of SEQ ID NO: 6; the KNG1 surrogate peptide comprises the amino acid sequence of SEQ ID NO: 7; and the MMP1 surrogate peptide comprises the amino acid sequence of SEQ ID NO: 8;
      (b-2) labeling the at least two surrogate peptides of step (b-1) by isotope;
      (b-3) digesting the biological sample by means of a proteolytic process to produce a digest;
      (b-4) adding a pre-determined concentration of the labeled versions of the surrogate polypeptides to the digest of the step (b-3);
      (b-5) measuring the amounts of the surrogate peptides and the labeled versions of the surrogate peptides in the mixture of step (b-4) by mass spectrometry;
      (b-6) dividing the measured amounts of the surrogate peptides by the measured amounts of the labeled versions of the surrogate peptides to obtain a ratio; and
      (b-7) determining the concentration of the target polypeptides in the biological sample based on the ratio of step (b-6) and the pre-determined concentration of the labeled versions of the surrogate peptides of step (b-4);
   (c) calculating a risk score based on the concentrations of the at least two target polypeptides determined in the step (b); and
   (d) determining whether the subject has or is at risk of developing OSCC based on the risk score of the step (c).

2. The method of claim 1, wherein the risk score is calculated by use of logistic regression.

3. The method of claim 2, wherein the risk score is calculated by the equation of:

$$\text{risk score} = \frac{e^{a+b1X1+b2X2+b3X3+b4X4}}{1+e^{a+b1X1+b2X2+b3X3+b4X4}}$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1.

4. The method of claim 3, wherein
when the risk score is lower than 0.4, then the subject does not have OSCC or is at low risk of developing OSCC; and
when the risk score is or above 0.4, then the subject has OSCC or is at high risk of developing OSCC.

5. The method of claim 1, wherein the biological sample is saliva.

6. A method of diagnosing and treating OSCC in a subject, comprising,
   (a) obtaining a sample from the subject;
   (b) determining the concentration of at least two target polypeptides in the biological sample by the steps of:
      (b-1) selecting at least two surrogate peptides corresponding to the at least two target polypeptides, wherein each of the at least two surrogate peptides is selected from the group consisting of ANXA2 surrogate peptide, HSPA5 surrogate peptide, KNG1 surrogate peptide, and MMP1 surrogate peptide, wherein the ANXA2 surrogate peptide comprises the amino acid sequence of SEQ ID NO: 5; the HSPA5 surrogate peptide comprises the amino acid sequence of SEQ ID NO: 6; the KNG1 surrogate peptide comprises the amino acid sequence of SEQ ID NO: 7; and the MMP1 surrogate peptide comprises the amino acid sequence of SEQ ID NO: 8;
      (b-2) labeling the at least two surrogate peptides of step (b-1) by isotope;
      (b-3) digesting the biological sample by means of a proteolytic process to produce a digest;
      (b-4) adding a pre-determined concentration of the labeled versions of the surrogate polypeptides to the digest of the step (b-3);

(b-5) measuring the amounts of the surrogate peptides and the labeled versions of the surrogate peptides in the mixture of step (b-4) by mass spectrometry;

(b-6) dividing the measured amounts of the surrogate peptides by the measured amounts of the labeled versions of the surrogate peptides to obtain a ratio; and (b-7) determining the concentration of the target polypeptides in the biological sample based on the ratio of step (b-6) and the pre-determined concentration of the labeled versions of the surrogate peptides of step (b-4);

(c) calculating a risk score based on the concentration of the at least two target polypeptides determined in the step (b); and (d) subjecting the subject to an anti-cancer treatment, if the risk score of the subject determined from the step (c) is or above 0.4.

7. The method of claim 6, wherein the anti-cancer treatment is surgical removal of OSCC.

8. The method of claim 6, wherein the risk score is calculated by use of logistic regression.

9. The method of claim 8, wherein the risk score is calculated by an equation of:

$$\text{risk score} = \frac{e^{a+b1X1+b2X2+b3X3+b4X4}}{1+e^{a+b1X1+b2X2+b3X3+b4X4}}$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1.

10. The method of claim 6, wherein the biological sample is saliva.

11. A method of determining whether a biological sample comprises cancerous oral squamous cells, comprising, (a) determining the concentration of at least two target polypeptides in the biological sample by the steps of (a-1) selecting at least two surrogate peptides corresponding to the at least two target polypeptides, wherein each of the at least two surrogate peptides is selected from the group consisting of ANXA2 surrogate peptide, HSPA5 surrogate peptide, KNG1 surrogate peptide, and MMP1 surrogate peptide, wherein the ANXA2 surrogate peptide comprises the amino acid sequence of SEQ ID NO: 5; the HSPA5 surrogate peptide comprises the amino acid sequence of SEQ ID NO: 6; the KNG1 surrogate peptide comprises the amino acid sequence of SEQ ID NO: 7; and the MMP1 surrogate peptide comprises the amino acid sequence of SEQ ID NO: 8;

(a-2) labeling the at least two surrogate peptides of step (a-1) by isotope;

(a-3) digesting the biological sample by means of a proteolytic process to produce a digest;

(a-4) adding a pre-determined concentration of the labeled versions of the surrogate polypeptides to the digest of the step (a-3);

(a-5) measuring the amounts of the surrogate peptides and the labeled versions of the surrogate peptides in the mixture of step (a-4) by mass spectrometry;

(a-6) dividing the measured amounts of the surrogate peptides by the measured amounts of the labeled versions of the surrogate peptides to obtain a ratio; and (a-7) determining the concentration of the target polypeptides in the biological sample based on the ratio of step (a-6) and the pre-determined concentration of the labeled versions of the surrogate peptides of step (a-4);

(b) calculating a risk score based on the concentration of the at least two target polypeptides determined in the step (a); and (c) assessing whether the biological sample comprises cancerous oral squamous cells based on the risk score of the step (b).

12. The method of claim 11, wherein the risk score is calculated by use of logistic regression.

13. The method of claim 12, wherein the risk score is calculated by an equation of:

$$\text{risk score} = \frac{e^{a+b1X1+b2X2+b3X3+b4X4}}{1+e^{a+b1X1+b2X2+b3X3+b4X4}}$$

wherein e is a mathematical constant that is the base of the natural logarithm; a is a constant value; X1, X2, X3 and X4 respectively represent the concentrations of ANXA2, HSPA5, KNG1 and MMP1; and b1, b2, b3 and b4 respectively represent the coefficient of variation of ANXA2, HSPA5, KNG1 and MMP1.

14. The method of claim 13, wherein when the risk score is or above 0.4, then the biological sample comprises cancerous oral squamous cells.

15. The method of claim 11, wherein the biological sample is saliva.

\* \* \* \* \*